(12) United States Patent
Ravansari

(10) Patent No.: US 11,467,150 B2
(45) Date of Patent: Oct. 11, 2022

(54) SYSTEM AND METHOD FOR SOIL CHARACTERIZATION

(71) Applicant: X-Centric Sciences Inc., San Diego, CA (US)

(72) Inventor: Roozbeh Ravansari, Armidale (AU)

(73) Assignee: X-Centric Sciences Inc., San Diego, CA (US)

( * ) Notice: Subject to any disclaimer, the term of this patent is extended or adjusted under 35 U.S.C. 154(b) by 113 days.

(21) Appl. No.: 16/792,187

(22) Filed: Feb. 14, 2020

(65) Prior Publication Data

US 2020/0264153 A1 Aug. 20, 2020

Related U.S. Application Data

(60) Provisional application No. 62/900,656, filed on Sep. 16, 2019, provisional application No. 62/891,353, filed on Aug. 25, 2019, provisional application No. 62/805,315, filed on Feb. 14, 2019.

(51) Int. Cl.
*G01N 33/24* (2006.01)
*G01N 21/3563* (2014.01)

(52) U.S. Cl.
CPC ......... *G01N 33/24* (2013.01); *G01N 21/3563* (2013.01)

(58) Field of Classification Search
CPC ... G01N 33/24; G01N 21/3563; G01N 23/223
See application file for complete search history.

(56) References Cited

U.S. PATENT DOCUMENTS

| | | | |
|---|---|---|---|
| 5,306,909 A * | 4/1994 | Jones | G01N 21/3577 250/255 |
| 2006/0023213 A1* | 2/2006 | Funakubo | G01N 21/211 356/369 |
| 2017/0122889 A1* | 5/2017 | Weindorf | G01N 21/3563 |

OTHER PUBLICATIONS

Adams, W.A., 1973. The Effect of Organic Matter on the Bulk and True Densities of Some Uncultivated Podzolic Soils. Journal of Soil Science 24(1), 10-17.

(Continued)

*Primary Examiner* — Bryan Bui
(74) *Attorney, Agent, or Firm* — Hamilton, Brook, Smith & Reynolds, P.C.

(57) ABSTRACT

A system and method for characterizing matter, for example, soil organic content is disclosed. A radiation and electric field sensor measure sample properties before, during and after irradiation. Calibrations are developed relating those measurements to useful properties of matter, for example, soil density and organic content. As an example of an embodiment of the disclosed invention an instrument attachment for portable X-ray fluorescence instrumentation was prototyped enabling concurrent volumetric soil organic matter quantification. This primary prototype outperformed more expensive emerging visible-near infrared multivariate instrumentation using parsimonious soil specific simple linear regression (R2 ranged 0.85-0.97) enabling rapid, parallel, nondestructive, cost-effective acquisition of soil elemental concentrations together with organic content data.

20 Claims, 11 Drawing Sheets

(56) References Cited

OTHER PUBLICATIONS

Jarvis, M., 2011. "Science Selects 'Science Buddies' Web site to Win SPORE Award," American Association for the Advancement of Science (AAAS), I Available at: https://www.aaas.org/news/science-selects-science-buddies-web-site-win-spore-award [Accessed: Apr. 29, 2019]. (Apr. 29).

Anderson, C., 2013. Maker Movement, Wired. Conde Nast Publications, Inc., San Francisco, pp. 106-n/a.

Assuncao, S.A., Pereira, M.G., Rasset, J.S., Berbara, R.L.L., Garcfa, A.C., 2019. Carbon input and the structural quality of soil organic matter as a function of agricultural management in a tropical climate region of Brazil. Science of The Total Environment 658, 901-911.

Australia New Zealand Banking Group—ANZ, 2018. Carbon Trading—ANZ I Available at: http://www.anz.com/corporate/markets/carbon-trading/ [Accessed: Aug. 21, 2018]. (Aug. 21, 2018).

Australian Federal Government—Australia, 2018. Carbon Credits (Carbon Farming Initiative—Measurement of Soil Carbon Sequestration in Agricultural Systems) Methodology Determination 2018 F2018L00089 Available at: https://www.legislation.gov.au/Series/F2018L00089 [Accessed: Aug. 21, 2018].

Bentler, P.M., Mooijaart, A., 1989. Choice of structural model via parsimony: A rationale based on precision. Psychological Bulletin 106(2), 315-317.

DAFWA, 2013. Report card on sustainable natural resource use in Agriculture, Australian Department of Agriculture and Food Western Australia.

Galuszka, A., Migaszewski, Z.M., Namiesnik, J., 2015. Moving your laboratories to the field—Advantages and imitations of the use of field portable instruments in environmental sample analysis. Environmental Research 140, 593-603.

IUSS Working Group, W., 2006. World reference base for soil resources. World Soil Resources Report 103.

Kwon, 8.-R., Lee, J., 2017. What makes a maker: the motivation for the maker movement in ICT. Information Technology for Development 23(2), 318-335.

Lal, R., 2006. Enhancing crop yields in the developing countries through restoration of the soil organic carbon pool in agricultural lands. Land Degradation & Development 17(2), 197-209.

Parsons, C., Margui Grabulosa, E., Pili, E., Floor, G.H., Roman-Ross, G., Charlet, L., 2013. Quantification of trace arsenic in soils by field-portable X-ray fluorescence spectrometry: Considerations for sample preparation and measurement conditions. Journal of Hazardous Materials 262(Supplement C), 1213-1222.

Potts, P.J., West, M., 2008. Portable X-ray Fluorescence Spectrometry: Capabilities for in Situ Analysis. RSC Pub.

Ravansari, R., Lemke, L.D., 2018. Portable X-ray fluorescence trace metal measurement in organic rich soils: pXRF response as a function of organic matter fraction. Geoderma 319, 175-184.

Reeves, D.W., 1997. The role of soil organic matter in maintaining soil quality in continuous cropping systems. Soil and Tillage Research 43(1), 131-167.

Rouillon, M., Taylor, M.P., 2016. Can field portable X-ray fluorescence (pXRF) produce high quality data for application in environmental contamination research? Environmental Pollution 214(Supplement C), 255-264.

Rouillon, M., Taylor, M.P., Dong, C., 2017. Reducing risk and increasing confidence of 1002 decision making at a lower cost: In-situ pXRF assessment of metal-contaminated sites. Environmental Pollution 229, 780-789.

Rumpel, C., Amiraslani, F., Koutika, L.-S., Smith, P., Whitehead, D., Wollenberg, E., 2018. Put more carbon in soils to meet Paris climate pledges. Nature 564.

Saini, G.R., 1966. Organic Matter as a Measure of Bulk Density of Soil. Nature 210(5042), 1295-1296.

Science Buddies Staff, 2017. How to Build an X-ray Machine I Available at: https://www.sciencebuddies.org/science-fair-projects/project-ideas/Phys_p083/physics/how-to-build-an-x-ray-machine#summary [Accessed: Apr. 28, 2019], (Apr. 28).

Sedlak, D.L., 2018. Disruptive Environmental Research. Environmental Science & Technology 52(15), 8059-8060.

Soriano-Disla, J.M., Janik, L.J., Viscana Rossel, R.A., Macdonald, L.M., McLaughlin, M.J., 2014. The Performance of Visible, Near-, and Mid-Infrared Reflectance Spectroscopy for Prediction of Soil Physical, Chemical, and Biological Properties. Applied Spectroscopy Reviews 49(2), 139-186.

Taylor, P.O., Ramsey, M.H., Potts, P.J., 2004. Balancing Measurement Uncertainty against Financial Benefits: Comparison of In Situ and Ex Situ Analysis of Contaminated Land. Environmental Science & Technology 38(24), 6824-6831.

UNFCCC, 2016. Paris Agreement—Status of Ratification I UNFCCC—United Nations Framework for Convention on Climate Change Available at: https://unfccc.int/process/the-paris-agreement/status-of-ratification [Accessed Aug. 21, 2018]. (Aug. 21, 2018).

USEPA, 1998. Environmental technology verification report. Field portable X-ray fluorescence analyzer. Metorex XMET 920-P and 940, EPA/600/R-97/146, United States Environmental Protection Agency.

Van Groenigen, J.W., van Kessel, C., Hungate, B.A., Oenema, 0., Powlson, D.S., van Groenigen, K.J., 2017. Sequestering Soil Organic Carbon: A Nitrogen Dilemma. Environmental Science & Technology 51 (9), 4738-4739.

Viscarra Rossel, R.A., McGlynn, R.N., McBratney, A.B., 2006. Determining the composition of mineral-organic mixes using UV-vis-NIR diffuse reflectance spectroscopy. Geoderma 137(1), 70-82.

Wang, D., Chakraborty, S., Weindorf, D.C., Li, B., Sharma, A., Paul, S., Ali, M.N., 2015. Synthesized use of VisNIR DRS and PXRF for soil characterization: Total carbon and total nitrogen. Geoderma 243-244(Supplement C), 157-167.

B. A. Schumacher, K. C. Shines, J. V. Burton, M. L. Papp, Comparison of Three Methods For Soil Homogenization. Soil Science Society of America Journal 54, 1187-1190 (1990).

ASTM, ASTM Method 02974-14: Standard Test Methods for Moisture, Ash, and Organic Matter of Peat and Other Organic Soils. (2014).

B. R. Wilson, D. King, I. Growns, M. Veeragathipillai, Climatically driven change in soil carbon across a basalt landscape is restricted to non-agricultural land use systems Soil Research 55, 376-388 (2017).

C. Kilbride, J. Poole, T. R. Hutchings, A comparison of Cu, Pb, As, Cd, Zn, Fe, Ni and Mn determined by acid exlraction/ICP-OES and ex situ field portable X-ray fluorescence analyses. Environmental Pollution 143, 16-23 (2006).

N. Brand, C. Brand, Performance comparison of portable XRF instruments. Geochemistry: Exploration, Environment, Analysis, 2012-2172 (2014).

M. Ellinger, I. Merbach, U. Werban, M. LieB, Error propagation in spectrometric functions of soil organic carbon. SOIL Discuss. 2019, 1-25 (2019).

T. C. Kenna et al., Evaluation and calibration of a Field Portable X-Ray Fluorescence spectrometer for quantitative analysis of siliciclastic soils and sediments. Journal of Analytical Atomic Spectrometry 26, 395-405 (2011).

R. D. Cook, Influential observations in linear regression. Journal of the American Statistical Association 74, 169-174 (1979).

USEPA, "EPA Method 6200 Field Portable X-Ray Fluorescence Spectrometry for the Determination of Elemental Concentrations in Soil and Sediment," (United States Environmental Protection Agency, 2007).

R. H. Redus, J. A. Pantazis, T. J. Pantazis, A. C. Huber, B. J. Cross, Characterization of CdTe detectors for quantitative X-ray spectroscopy. IEEE Transactions on Nuclear Science 56, 2524-2532 (2009).

R. Redus, A. Huber, J. Pantazis, T. Pantazis, D. Sperry, in Nuclear Science Symposium Conference Record, 2006. IEEE. (IEEE, 2006), vol. 6, pp. 3794-3797.

J. Wetterlind, B. Stenberg, Near-infrared spectroscopy for within-field soil characterization: small local calibrations compared with national libraries spiked with local samples. European Journal of Soil Science 61, 823-843 (2010).

* cited by examiner

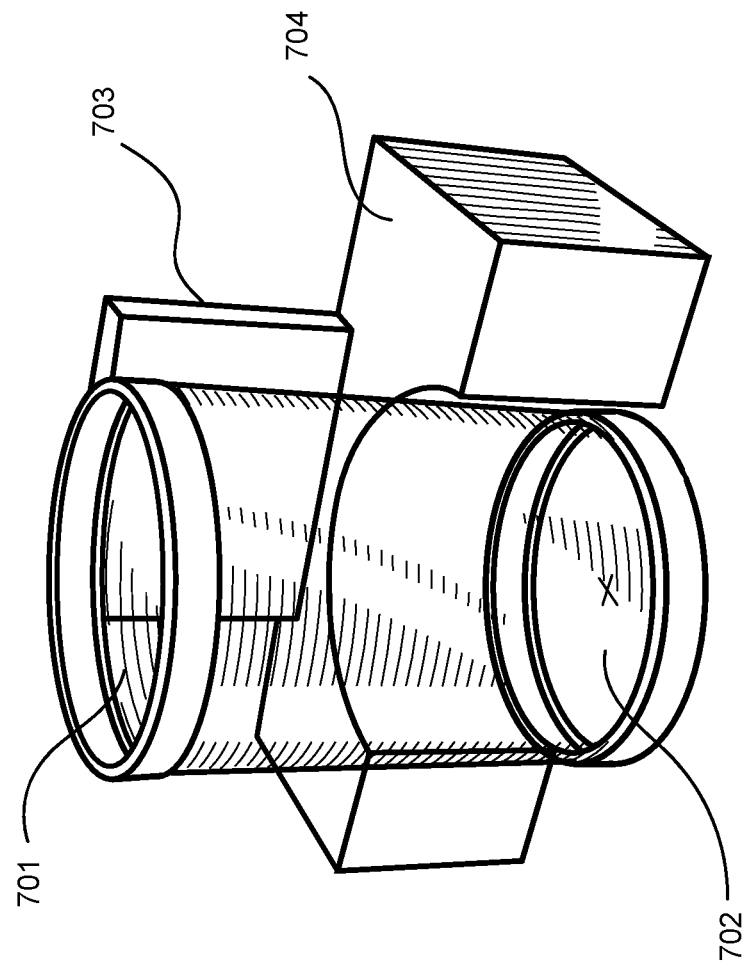
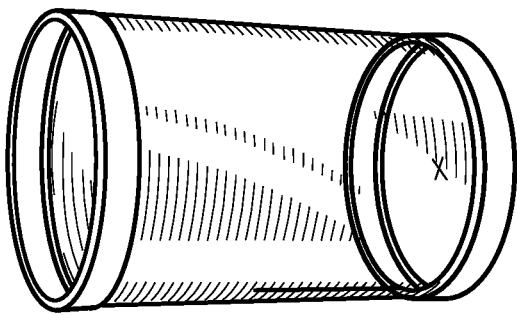
FIG. 7B
FIG. 7A

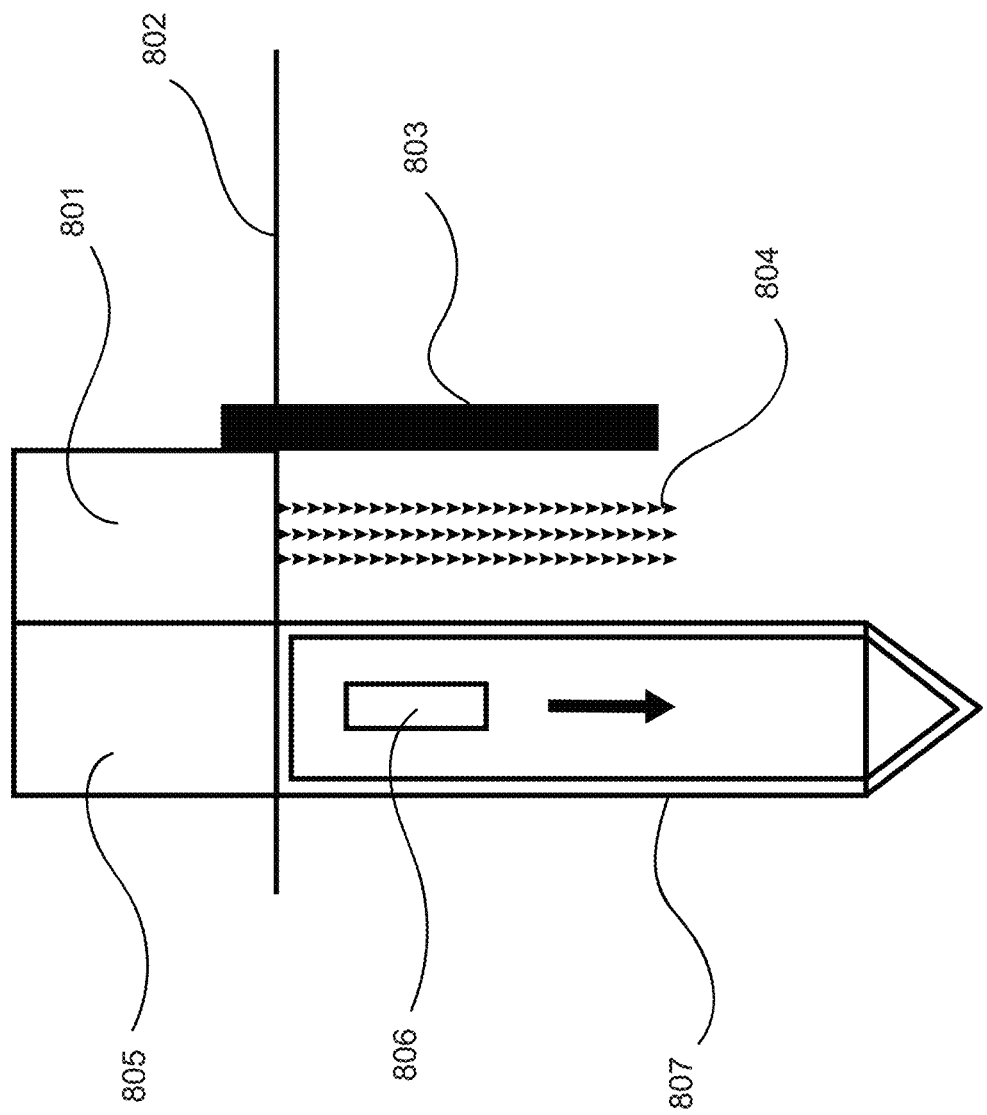

SYSTEM AND METHOD FOR SOIL CHARACTERIZATION

CROSS-REFERENCE TO RELATED APPLICATIONS

The present application claims priority to United States provisional patent application Nos. 62/900,656, filed on Sep. 16, 2019, 62/891,353, filed on Aug. 25, 2019, and 62/805,315, filed on Feb. 14, 2019, disclosures of which are incorporated herein at least by reference.

STATEMENT REGARDING FEDERALLY SPONSORED RESEARCH

Not Applicable

THE NAMES OF THE PARTIES TO A JOINT RESEARCH AGREEMENT

Not Applicable

STATEMENT REGARDING PRIOR DISCLOSURES BY THE INVENTOR OR A JOINT INVENTOR

Not Applicable

FIELD OF THE INVENTION

The present invention is in the field of matter chemical and/or property characterization.

BACKGROUND OF THE INVENTION

Development of innovative and disruptive environmental technologies are needed to address the ever-increasing evolving environmental threats the Earth and its inhabitants face such as climate change. The United Nations Framework Convention on Climate Change (UNFCCC) recently introduced the 4-per-1000 (4p1000) initiative in the Paris Agreements at the 21st Conference of Parties (COP21 Nov. 2015); 179 of the 197 member country signatories have ratified the agreement and it came into force as of November-2016 (UNFCCC, 2016). The 4p1000 initiative aims to mitigate climate change by increasing agricultural soil organic carbon (SOC) by 0.4% per year thereby reducing atmospheric $CO_2$ (van Groenigen et al., 2017). As corollary, some countries are implementing or modifying legislative framework incentivizing carbon farming by providing subsidies or value for verified increases in SOC, making carbon farming potentially lucrative for farmers and landowners. For example, in Australia the "Carbon Credits-Carbon Farming Initiative-F2018L00089" came into force January-2018 (Australian Federal Government—Australia, 2018). The Australia New Zealand Banking Group has also announced a carbon trading desk to accommodate the young carbon markets and allows consumers or corporate entities to sell earned credits, purchase credits to offset carbon emissions, or trade credits as investment options (Australia New Zealand Banking Group—ANZ, 2018). Carbon farming is doubly advantageous for farmers because they can reap governmental incentives while increasing their soil quality and ultimately, product yields (Rumpel et al., 2018). Economically measuring and monitoring soil characteristics such as SOC is critical in all of these initiatives, and advances in rapid assessment instrumentation and techniques are needed to address evolving global policy, climate change mitigation and monitoring needs. For example, climate scientists, environmental scientists and agriculturalists require quantification of SOM and SOC because of the critical influence on many factors including pollution risk, nutrient bioavailability, agricultural productivity and climate change (DAFWA, 2013; Lal, 2006; Reeves, 1997; van Groenigen et al., 2017).

Soil properties such as soil organic matter (OM) and SOC are typically quantified using destructive wet oxidation, loss on ignition (LOI) or dry combustion (DC) techniques which are time consuming, costly, or produce environmentally harmful byproducts (Assunção et al., 2019; Rumpel et al., 2018; Soriano-Disla et al., 2014; Wang et al., 2015). In science and statistics simplicity and parsimoniousness is desired from models (Bentler and Mooijaart, 1989), i.e. the least complex model that sufficiently describes observed phenomenon is desired. Emerging multivariate spectroscopy methods and instruments such as visible near infrared (Vis-NIR), mid-infrared (MIR), or Fourier transform infrared (FTIR) devices have been used to characterize SOC (Assunção et al., 2019; Rumpel et al., 2018; Soriano-Disla et al., 2014; Wang et al., 2015). Such chemometric and multivariate reliant instrumentation develop models that are less statistically parsimonious compared to simple linear regression (SLR) models because multivariate methods utilize multiple predictors whereas SLR utilizes a single independent variable. These spectroscopy techniques are also limited to sample surfaces and do not analyze sample volumetric composition. Portable X-ray fluorescence (XRF) is another example of a rapid, mobile, non-destructive, high throughput and economical device well suited for investigations where many samples must be analyzed and/or dense characterization of within site spatial variability in geochemical composition is needed (Rouillon and Taylor, 2016; Rouillon et al., 2017; Taylor et al., 2004). Portable XRF can be employed both in-situ or ex-situ and possesses the advantage of producing measurements based on elementally and matrix dependent volumes of analyses (Ravansari and Lemke, 2018). Portable XRF devices however cannot quantify light elements which are the main constituents of SOM and SOC (e.g. carbon, oxygen), and thus they cannot be used to directly quantify these parameters via parsimonious simple linear regression (Ravansari and Lemke, 2018). Attempts at combining PXRF and Vis-NIR (e.g. United States patent U.S. Ser. No. 15/319,816) data increase predictive power (Wang et al., 2015) of multivariate methods but move away from cost-efficiency and simplification. Adapting PXRF devices at low cost to generate information such as SOM or SOC in addition to other information so would significantly advance capacity and meet the needs of parties with a vested interest in soil characterization (e.g. farmers or soil scientists).

Therefore, disruptive environmental innovation is needed to decrease the cost of environmental monitoring and sample characterization to address the increasingly complex problems humanity faces (Sedlak, 2018). This patent details the advancement of existing PXRF technology using novel sensor integrations which enable parallel auxiliary data acquisition during regular analyses. This additional data can be used to better characterize soil chemical characteristics than what is possible with PXRF alone.

SUMMARY OF THE INVENTION

The present invention discloses novel means of obtaining additional sample information in parallel to portable X-ray fluorescence measurements. Such information is obtained by positioning an electric field sensor near or within a sample undergoing radiation bombardment (via intrusive electrodes, contactless electrodes, electric field sensors, or otherwise). The electric field is measured before (to establish a baseline), during (to observe variation over time) and after irradiation ceases (to measure the final electric field and the subsequent relaxation and attenuation of the sample's electric field over time). These electric field measurements are calibrated to one or more of the sample's properties such as soil organic content. Different atoms possess different fluorescence and electron yields with lighter elements possessing very high electron yields. There exists an inverse relationship between fluorescence yield and electron yield for elemental K-alpha emissions which is one of the reasons it is difficult to obtain a good signal for light elements using the X-ray fluorescence method (light element fluorescence yields are low and electron yields are high). The electric properties of a sample may vary depending on the sample's composition as electrons are excited or knocked off the sample during radiation bombardment (which may generate an electric field, voltage or potential). This information is indicative of a sample's properties such as but not limited to soil organic content.

The present invention discloses a novel portable X-ray fluorescence instrument no attachment to further obtain additional sample information in parallel to portable X-ray fluorescence analyses by positioning a radiation sensor adjacent to a sample undergoing radiation bombardment. The radiation escaping the sample undergoing bombardment is measured and related to one or more properties of the sample such as density or organic content.

The present invention also discloses a novel means of disturbing or standardizing a non-solid sample such as soil or water by utilizing a surface transducer to send vibrational energy through a sample.

The present invention also discloses a novel calibration method whereby more accurate results can be achieved using multivariate or neural network models by predicting correction coefficients to be applied to measurements obtained using simpler methods (as opposed to predicting analytes directly using such multivariate and neural network models).

In an embodiment, for ex-situ analyses samples are obtained from the field and bagged and tagged with an NFC sticker that has data such as GPS, date, time, sampler name, or other data written to it using a device such as a mobile phone. The sample can then be brought back to a lab, processed and analyzed with the data being written or appended directly to the NFC chip in addition to potential upload to a network connected database. This has the advantage that the data is directly accessible to any NFC enabled device, either connected to a network or not connected to the network since information is directly available on the NFC tag. A device such as a phone, mobile application is used to transfer GPS, date, time and instrumental data directly to an NFC tag for field applications. The data is directly accessible to any NFC enabled device, either connected to a network or not connected to the network since the data is directly available on the NFC tag. For example, this is advantageous as opposed to having to associate a unique identifier with the relevant data. Instead, relevant data such as GPS locational information is directly stored on the sample itself via an adhesive or attached NFC tag on the sample or sample container which is accessible via any NFC reader device regardless of whether the reader is using a unique identifier to associate data to the sample, pulling or pushing data to or from a database via a network connection. The essential information is stored on the sample or sample container itself which is highly advantageous.

In another embodiment, the electric field of the sample is measured before, during and after bombardment by radiation using one or more intrusive electrodes which measure potential. They can be located adjacent to the area of irradiation such that the irradiating beam illuminates the sample and one or more intrusive electrodes are located on one or both sides of the irradiated area enabling measurement of the potential between these electrodes or if a single electrode is used, the potential with respect to some other reference, for example, voltage between the sample and ground.

In another embodiment, ambient environmental sensors (e.g. humidity, temperature, barometric pressure) are to be incorporated to log information which can be used by algorithms to account or correct for variability in electric field buildup and dissipation characteristics of the sample. For example, an electric field measurement conducted on a relatively humid day will lead to a faster dissipation of the charge build up and may affect measurements on the sample during and after bombardment leading to variability in measurement of the sample electric properties conducted on other days of variable humidity.

An embodiment of the present invention comprises a modular, clip on or attachable PXRF instrument attachment comprised of one or more of the following: a radiation detector, electric field sensor, transducer, NFC reader and/or writer.

An embodiment of the present invention comprises one or more of the following: a radiation source, electric field sensor, radiation detector, transducer, NFC reader and/or writer.

An embodiment of the present invention involves a version for in-situ applications comprising an intrusive radiation detector and electric field sensor that penetrates the soil profile.

In another embodiment, foregoing the PXRF and its associated data, a standalone system is used comprising a pyroelectric radiation generator, tube, or means of radiation production in conjunction with an electric field sensor and/or a radiation detector for obtaining information on one or more sample matter properties or characteristics. The radiation source's flux output can be monitored using a secondary radiation detector placed near the source's output and corrections applied to account for flux variability in instances where radiation flux may be inconsistent such as with pyroelectric X-ray generators.

In another embodiment, a core scanner is employed. The platform on which the sample (core) lays is larger to accommodate a soil core and the platform or components such as the X-ray generator, electric field sensor, or radiation sensor move relative to one another so that different areas of the core can be scanned with the invention (with the placement of a radiation detector or electric field detector adjacent to the core undergoing analysis).

In another embodiment, an insulated and ungrounded PXRF stand is employed. The PXRF stand or bench is insulated by means of a base which is elevated off the surface on which the PXRF rests using insulating pedestals. The device will allow for a longer lasting charge to build on the sample for better detection of the electric field sensor. Thus, in benchtop mode, it is useful in certain situations to electrically insulate the PXRF bench by not using grounded components, for example utilizing the PXRF on battery power or using special wires which will not ground the PXRF or bench via wires connected to ground. For example, wires connected to a laptop or PC are typically grounded when plugged in and use of such wires may be less advantageous that using special wires that do not complete a connection to ground.

In another embodiment, the analysis platform is comprised of entirely insulating material to allow better electric field buildup and detection. In the case where dangerous radiation is employed, the shielding will wrap around the components comprising the invention including the insulating material because insulating material may not be sufficient for shielding requirements. The shielding enclosure in which the sample rests during analyses can be covered either internally or both internally and externally with a layer of insulating material.

In another embodiment, a digital or manual grounding mechanism for grounding the sample and ungrounding the sample exists to reset the charge on the sample for successive repeated measurement. This will allow repeated electric field measurements to be taken on the sample.

In another embodiment, the transducer is in contact with the sample either directly or indirectly via a transducing medium and it turns on prior to, during or after analysis. This is done to disturb the sample and change the immediate matter within the analysis area of the sample being analyzed (to obtain more representative measurements or other characteristics of the sample for example, signals from different size fractions of particulate matter such as soil, since grain size fractionation may occur during vibration). This can also be done to standardize the sample's density and compaction characteristics prior to analysis for measuring matter characteristics such as soil organic content as described.

In another embodiment, a diffraction crystal is used to control incident energy of radiation bombardment for measuring sample electric properties before, during and after radiation bombardment. The diffraction crystal may be rotated to bombard the sample with different energies and measuring penetrating radiation or sample electric properties which may be related to one or more properties of matter such as soil organic content, for example. The electrons in atoms are excited by different energies and thus controlling the bombardment energy of incident radiation using for example, a diffraction crystal may affect the sample's electric properties in a way that is indicative of one or more sample properties such as composition.

BRIEF DESCRIPTION OF THE DRAWINGS

A variety of types and shapes of electric field sensors, radiation detectors and radiation sources, and transducers exists, therefore the types, shapes and relative sizes of these components are not limited to those depicted in the following figures. Furthermore, the geometries, assemblies and relative positioning of these depicted components with respect to one another are not limited to those portrayed in these FIGS. because detection of the relevant signals can be achieved using many different positional configurations.

Lexicographic note: The figures depicted in the drawings with page numbers starting with "Study" are associated with the study which was conducted and described in the detailed descriptions section of this disclosure. These figures are referenced by figure captions within the detailed description section. Drawings whose page numbers do not start with "Study" are captioned here and further referenced and described in the detailed descriptions.

FIG. 7A is another embodiment for an analysis container.

FIG. 7B is another embodiment for an analysis container which is fitted snugly into a groove on the frame of the analysis platform for consistency during analyses.

FIG. 8 is an embodiment for an ex-situ version of the invention where comprising intrusive detector.

DETAILED DESCRIPTION

The present invention is described in enabling detail in the following examples, which may represent more than one embodiment of the present invention. Terms such as "a", "the", and "an" may not refer to a single article but rather the general type of article to which the referenced article belongs.

Figure 1C:
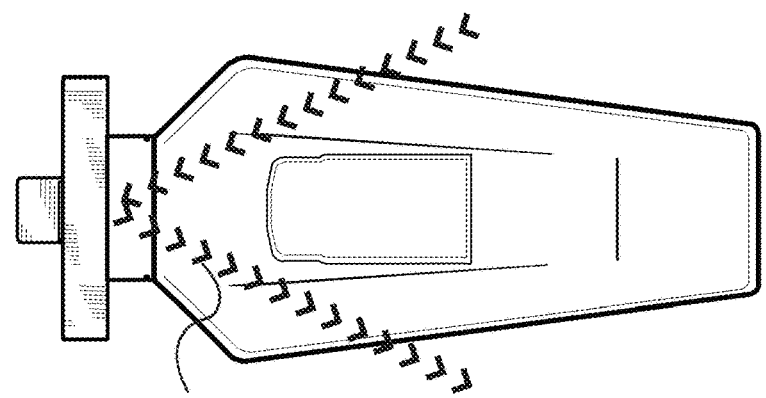
FIG. 1C is another view an embodiment of the PXRF instrument attachment.
Figure 1B:
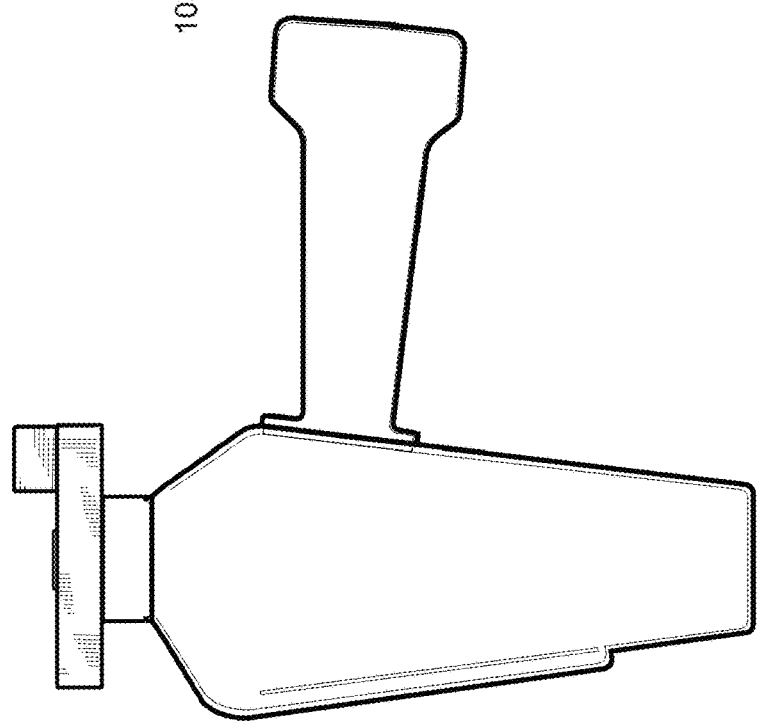
FIG. 1B is side view of an embodiment of the PXRF instrument attachment.
Figure 1A:
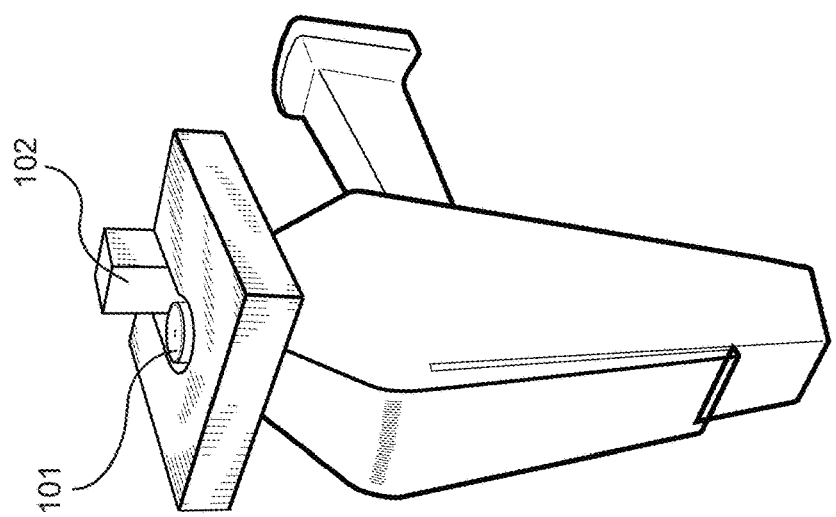
FIG. 1A an angled view of an embodiment of the PXRF instrument attachment.

FIG. 1A 101 is one example of the analysis vial which is analyzed by the PXRF. 102 can comprise the contactless electric field sensor and/or radiation detector. FIG. 1B can be a side view of the invention. FIG. 1C depicts another view of an example of the invention. 103 depicts an embodiment of the X-ray bombardment and detection of PXRF devices but these example shapes, geometries relative positions are not limiting.

Figure 2:
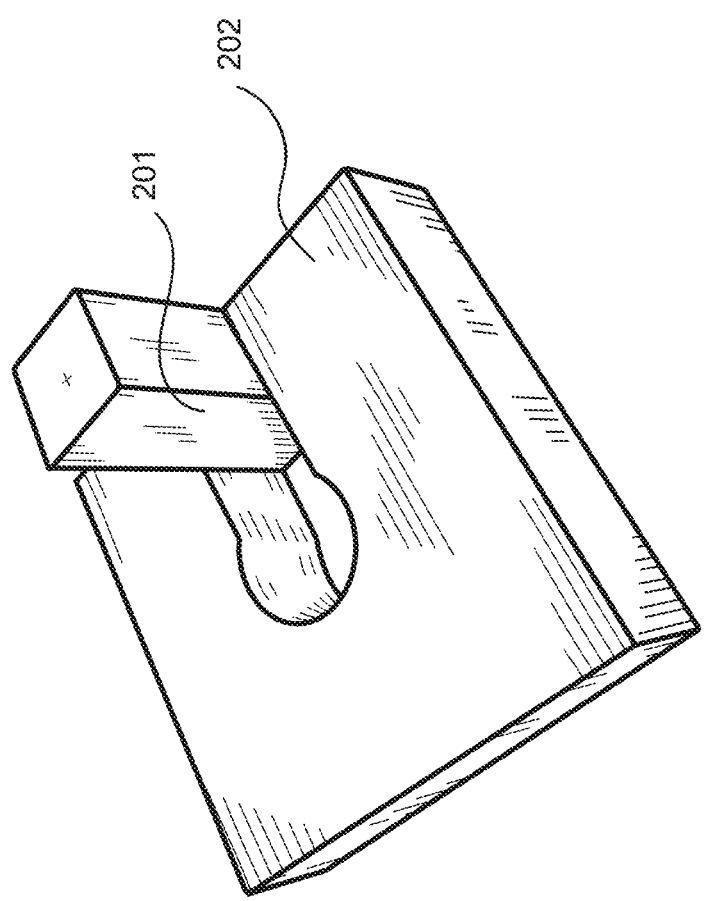
FIG. 2 is an embodiment for the frame containing the radiation detector and/or the electric field sensor.

FIG. 2 is one example of a PXRF instrument attachment frame comprising 201 which can be the radiation detector and/or the electric field detector. The groove in the frame 202 fits analysis containers so that the distance between the electric or radiation detectors and the sample undergoing analysis are consistent between all analyses.

Figure 3:
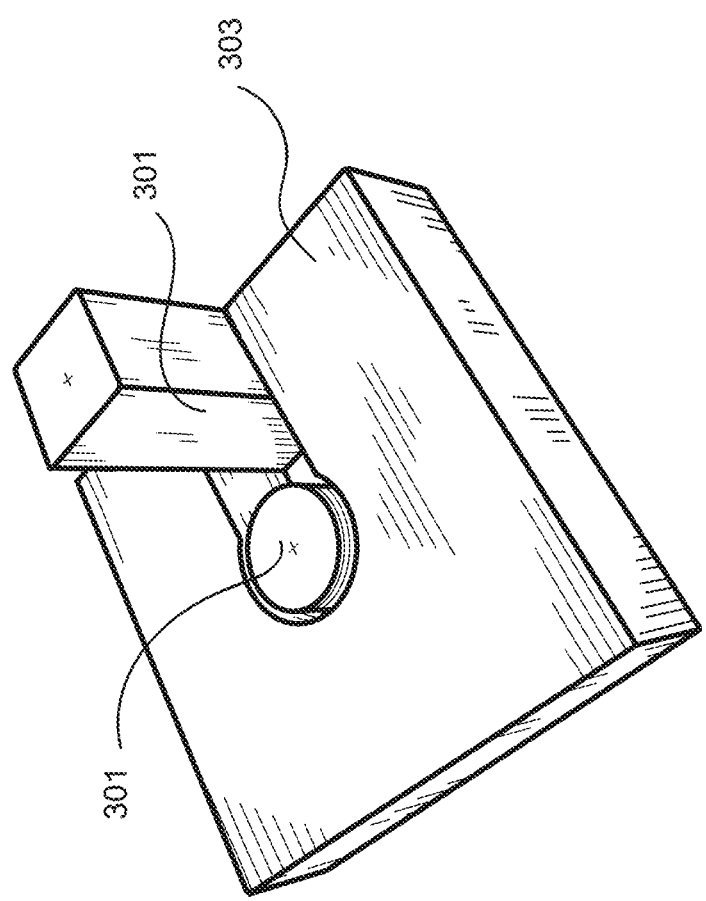
FIG. 3 is an embodiment for the frame comprising the invention which contains an analysis container.

FIG. 3 is one example of a PXRF instrument attachment frame 303 which is loaded with a container to be analyzed by the electric and/or radiation sensor(s).

Figure 4:
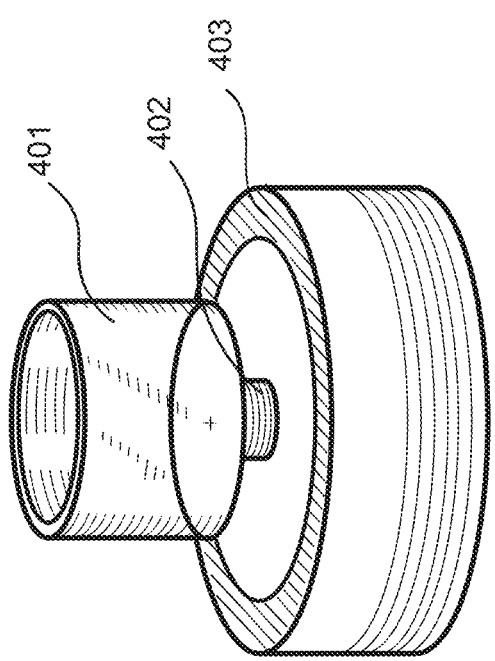
FIG. 4 is an embodiment for the transducer system described herein.

FIG. 4 is one example of an embodiment for the transducer system which is comprised of a transducer 403, the surface of the transducer 402 and a grove into which an analysis container can be placed for subsequent vibration of the sample. The transducer surface 402 can also be put in contact with the sample indirectly via a transducing medium, such as the PXRF instrument attachment frame, for example.

Figure 5:
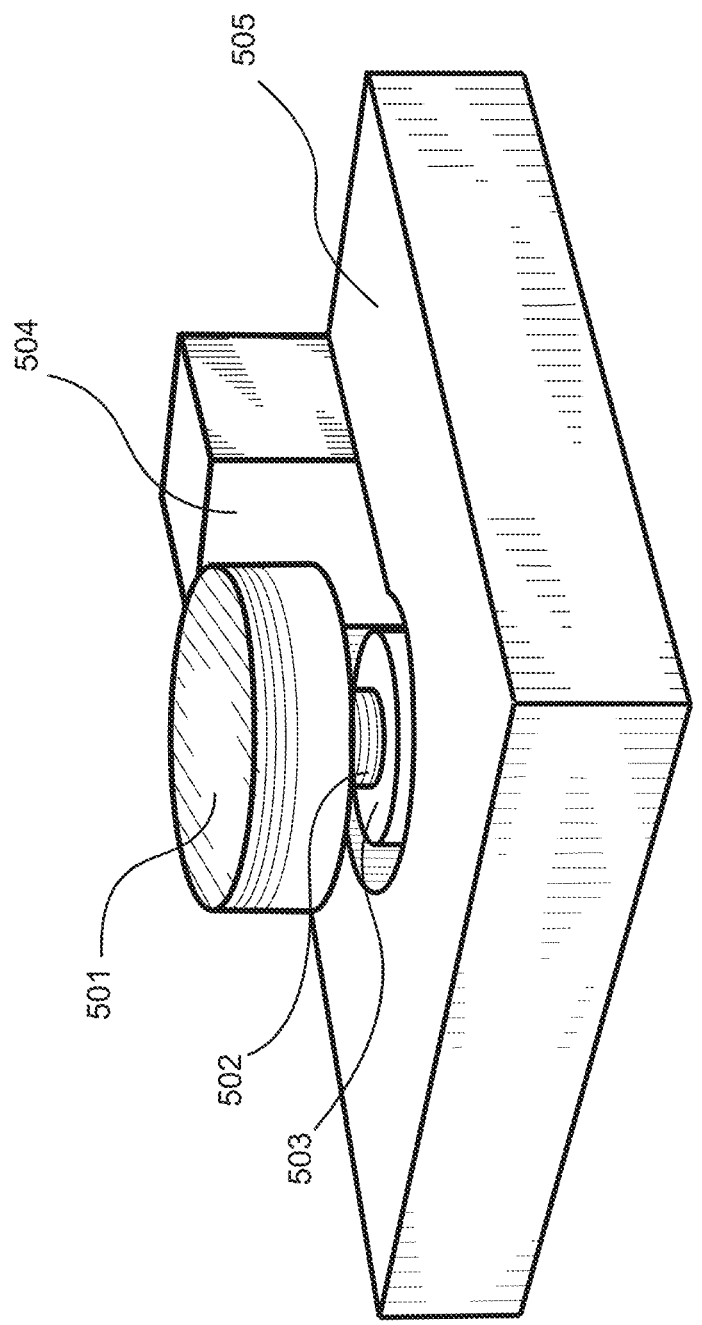
FIG. 5 is an embodiment for the transducer system which is in contact with the analysis vial.

FIG. 5 is one example of an embodiment for the transducer system's incorporation with the frame 505 comprised of the radiation detector and/or electric field detector 504. The transducer 501 is put into contact with the analysis container 503 and at some point before, during or after bombardment by radiation, vibrational energy is produced by the transducer 501 and transferred to the analysis container 503.

Figure 6B:
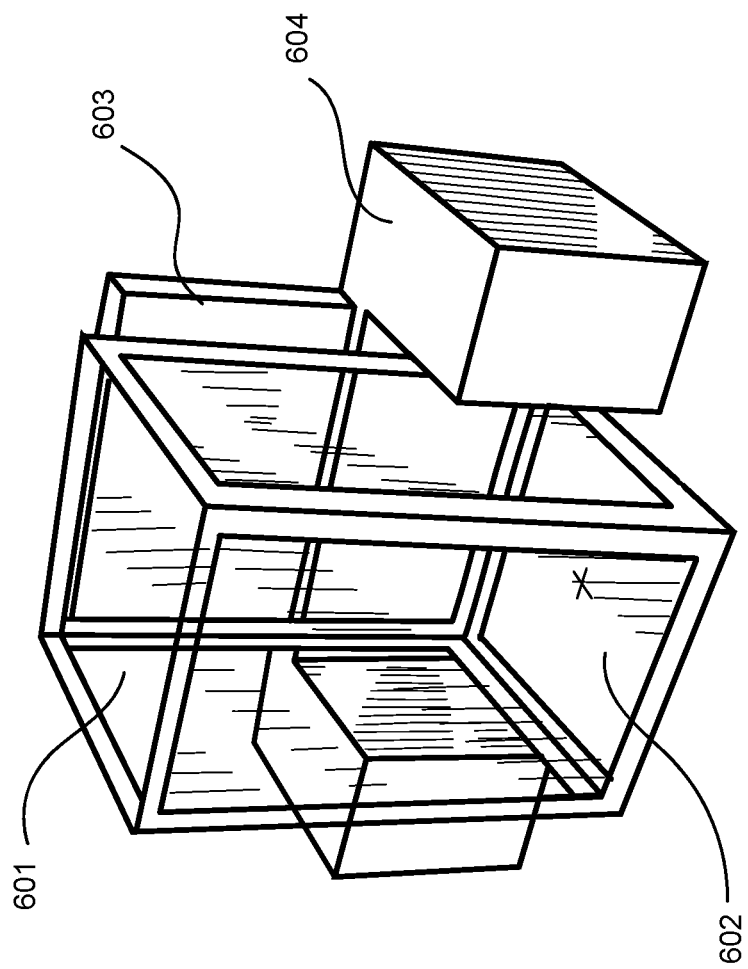
FIG. 6B is an embodiment for an analysis container that is fitted snugly into a groove on the frame for consistency during analyses.
Figure 6A:
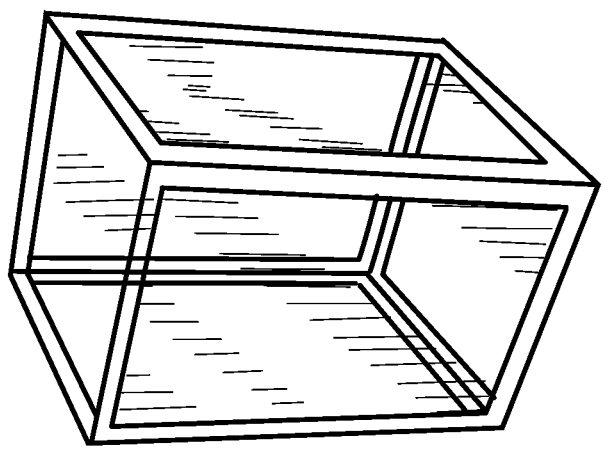
FIG. 6A is an embodiment for an analysis container.

FIG. 6A is an example of an analysis vial comprising of a non-permeable sidewall capable of containing for example, liquid or particulate matter such as water or soil.

FIG. 6B is an example of an analysis vial which fits snugly into a frame 604 to control distance and positioning of the analysis container 601 with respect to the electric and/or radiation detector(s) 603. The analysis container 601 possesses one or more thin but strong non-permeable sidewalls 602.

FIG. 7A is another example with a varying geometry of an analysis vial comprising of a non-permeable sidewall capable of containing for example, liquid or particulate matter such as water or soil.

FIG. 7B is an example of an analysis vial which fits snugly into a frame 704 to control distance and positioning of the analysis container 701 with respect to the electric and/or radiation detector(s) 703. The analysis container 701 possesses one or more thin but strong non-permeable sidewalls 702.

FIG. 8 is an example of an embodiment of the invention as an in-situ soil specific PXRF device in which example embodiments may be implemented. Pilot holes consisting of the exact dimensions of the intrusive enclosure 807 will be carved out of the soil 802 sampling spot by hammering hollow tube into the soil, this will prevent wear and tear on the protruding enclosure 807 by generating a hole into which the protruding X-Ray sensor enclosure 807 can fit into. The X-Ray source 801 tracks the sensor's 806 movement and moves with it to shoot irradiate the soil profile and shoot an X-ray beam 804 into the soil profile at the surface normal to the soil profile with the intrusive sensor 806 located adjacent to the X-Ray beam 804. It may also be possible to shoot the X-Ray beam 804 diagonally towards the detector for measurement of X-Ray attenuation properties of the soil. The sensor 806 itself can be stationary or it can move within the enclosure 807 enabling the acquisition of soil information including but not limited to soil density, and organic matter via attenuation measurements. It will also enable the acquisition of analyte concentrations at different depths within the soil profile thus mitigating problems arising from analyte vertical stratification (because the sensor 806 can move within its enclosure 807). The integrated water and temperature sensor 803 rendering volumetric water content coupled with density determinations are useful and may enable seamless calculation of one or more soil properties including gravimetric water content by the onboard electronics 805. The gravimetric water content will be used to seamlessly correct in-situ measurements for deviations caused by water effects via onboard computers and algorithm. Components of deviations in measurement accuracy caused by water effects and organic matter are further dealt with using the calibration method described herein. These methods used in concert enable total hydrofluoric digestion ICP quality data acquisition right in the field. Intrusive electrodes (not shown) will also penetrate the soil and they are located adjacent to the X-Ray beam such that the X-Ray beam is located in the center and intrusive electrodes are located on both sides of the X-Ray beam. This is done to measure soil electric properties before, during and after X-Ray bombardment. For light elements auger electron generation dominates when samples are bombarded by X-Rays. Thus, measurement of soil electric properties in samples before, during and after X-Ray bombardment via intrusive electrodes enables extraction of soil chemical information. Orchestration and integration of these sensors enable soil chemical characterization in a new novel and more effective manner than what is currently possible.

The embodiment of FIG. 8 may operate as follows:

a) Control and processing computer 805 initiates the emission of radiation from the radiation source.

b) The radiation source 801 irradiates the sample.

c) The radiation sensor 806 and other sensors (e.g., electric field sensor, X-ray sensor attached to the device as described above) detect the radiation traversing the sample or variations in soil properties before, during and after X-Ray bombardment.

d) During X-Ray bombardment, the X-Ray sensor situated within the enclosure moves to obtain soil chemical information from different areas of the soil sample undergoing analysis (vertical stratification information).

e) The sensors utilize the CPU 805 to log the information generated by all sensors to the memory.

f) The GPS generates spatial information associated with where the sample was analyzed.

g) The CPU 805 logs the information from the sensors and GPS to computer memory.

h) The CPU 805 uses the information obtained from the sensors and GPS to render useful soil information such as but not limited to soil water content, soil organic content, density, analyte concentrations, stratified analyte concentrations, and/or signals from different areas of the sample.

i) The information is logged to computer memory for future use and/or transferred to an online database or a computer database via wireless or a wired connection.

j) The rendered information is used to generate accurate XRF geochemical measurements by accounting for variability in matrix compositions via onboard CPU and/or computer algorithms or for other purposes.

Figure 9:
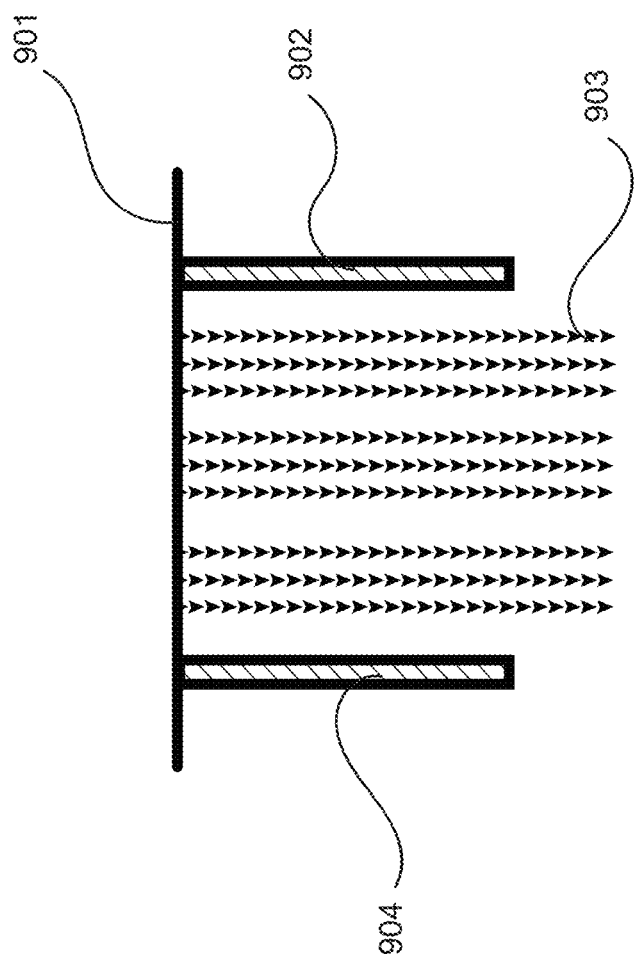
FIG. 9 is an embodiment of the intrusive electrodes placed adjacent to an irradiating beam for electric field measurement before, during and after radiation bombardment.

FIG. 9 is an example of the invention where intrusive electrodes penetrate a sample, for example, a soil profile 901, and the electric properties between the two electrodes 904 and 902 are measured before, during and after bombardment by radiation 903.

Figure 10:
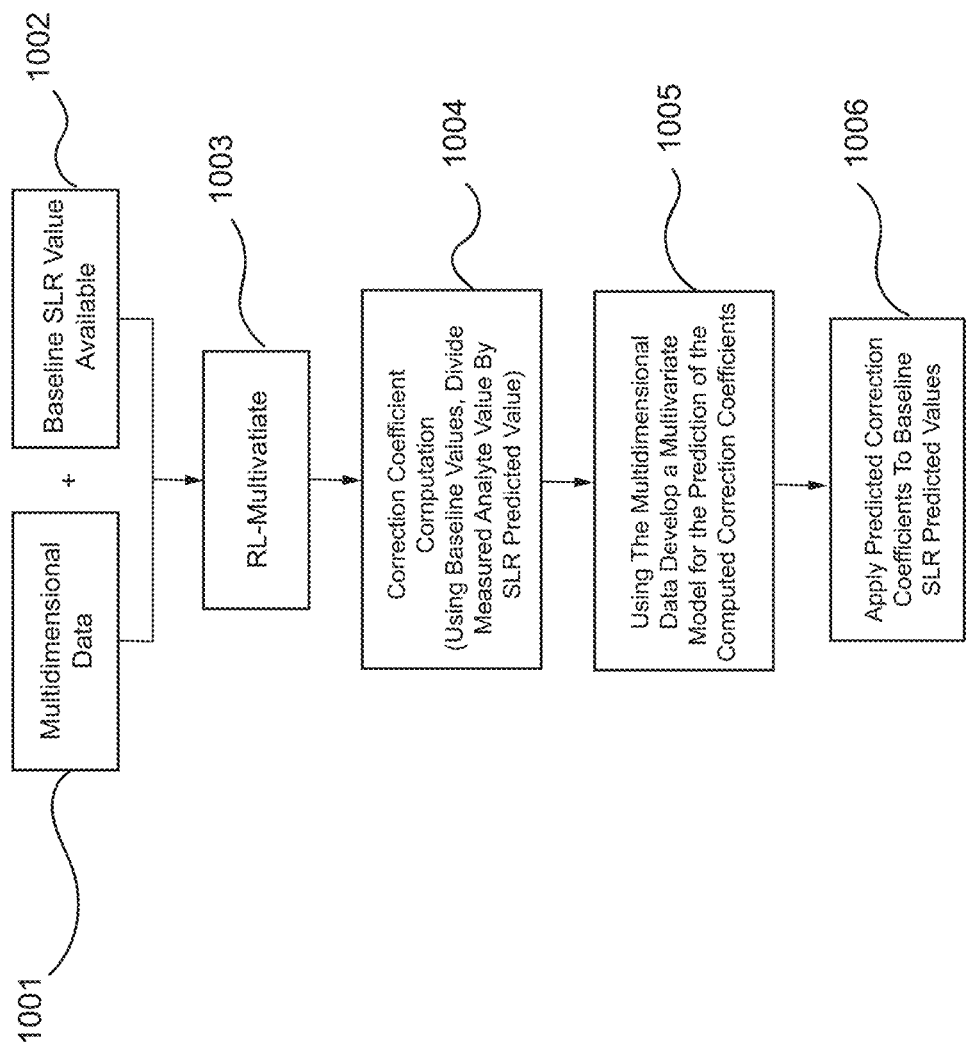
FIG. 10 is an embodiment of a method for calibrating measurements.

FIG. 10 is an example of the calibration method 1003 which may be employed if multidimensional data 1001 and some other analyte measurement 1002 is available. Correction coefficients may be computed 1004 using the available analyte concentration 1002 and predictive models developed for prediction of correction coefficients using multidimensional data 1005. These models can then be used on unknown samples to apply corrections to measurements rendered using other calibration models 1006.

Figure 11:
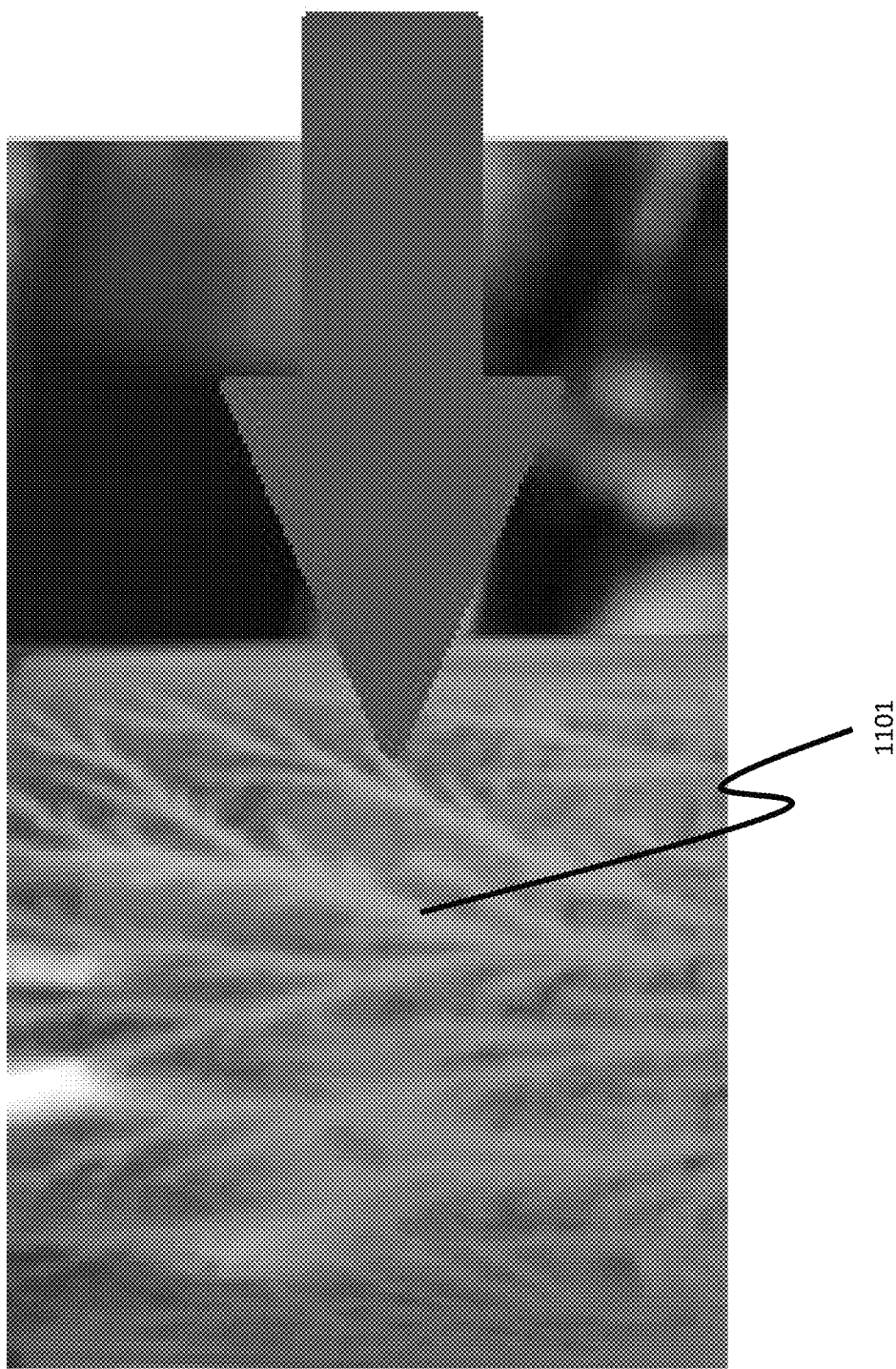
FIG. 11 depicts the residual electric discharge fractal pattern on an analysis vial which was bombarded by radiation during PXRF analyses. It is requested that this image be retained in color because the intricate fractal electric discharge pattern depicted on this photo cannot be appreciated in a black and white image.

FIG. 11 depicts the residual electric discharge fractal pattern 1101 on an analysis vial which was bombarded by radiation during PXRF analyses. Sample electric properties may change during bombardment therefore, electric properties may be detected before, during and after radiation bombardment and related to a sample's properties such as organic content, for example. The detected electric field may thus be indicative of a sample's properties such as soil organic content for example.

A non-limiting example of a study investigating some aspects of the present invention is now described. It will be apparent to the skilled artisan that the present invention may have other uses, for example, the analysis of other types of environmental samples such as geologic media or water or for the characterization of other properties of matter apart from the specific examples discussed here which are soil organic content and density. The descriptions of the relative positioning of the components comprising the present invention with respect to one another are non-limiting and are examples of specific embodiments. The settings, features and components used in this example study are non-limiting (such as analysis times, component operation settings, types of sensors, detectors, instruments, tube voltage, current, analysis times, and other).

Soil organic matter and organic carbon are variables of critical environmental importance in terms of soil productivity, global food security, and climate change mitigation. Rapid and accurate assessment of these variables is central to national programs and international agreements. Portable X-ray fluorescence instruments are widely used to rapidly quantify and map soil elements, however quantification of light elements comprising organic content is not yet possible. We developed a novel attachment for portable X-ray fluorescence instrumentation enabling concurrent volumetric soil organic matter quantification. This primary prototype outperformed more expensive emerging visible-near infrared multivariate instrumentation using parsimonious soil specific simple linear regression (R2 ranged 0.85-0.97) enabling rapid, parallel, nondestructive, cost-effective acquisition of soil elemental concentrations together with organic content data.

Theoretically, critical X-ray penetration depth is a function of a sample's bulk density (BD) and mass attenuation coefficient (Parsons et al., 2013; Potts and West, 2008). For soils, both BD and attenuation coefficient typically decrease as organic matter increases (Adams, 1973; Saini, 1966), therefore volumetric X-ray penetration is potentially confounded by both of these factors and an assessment of the importance of each was required to investigate the relationship between X-ray penetration and soil organic content. Data quality may also increase when the interplay and influence of these factors are accounted for in calibrations. Based on these principles, we developed an instrument attachment for PXRF which measures SOM by relating soil X-ray penetration to organic matter content. A Tracer III-SD PXRF (Bruker-United States of America) device was operated in benchtop mode and was fitted with a platform on which a Type V (Radiation Watch-Japan) radiation sensor was mounted. The sensor's photodiode was a X-100-7 100 mm2 PIN detector (First Sensor-Germany). The sensor was placed orthogonal to the PXRF analyzer surface area and adjacent to where samples are placed for analyses as shown in FIG. 1 (henceforth referred to as the Z-Plane sensor). We refer to the "Z-Plane sensor" as such because we have defined the PXRF analysis platform surface area as existing in the x and y plane and the sensor is situated orthogonally in the z-plane such that it captures otherwise egressing X-rays that escape through the analysis vial (FIG. 1). The detection of these X-rays at the Z-Plane sensor were indicative of a sample's organic content.

The PXRF was operated at 40 kV, 10 µA and samples were analyzed for 3 minutes each. Two soil types (Vertisol, Cambisol) (IUSS Working Group, 2006) and an unconsolidated sand were prepared by drying, grinding and sieving to the <250 µm fraction. The soils were then loaded with varying amounts of powdered and sieved (<250 µm) organic matter surrogates (Lucerne and sucrose). Samples were spiked with either Lucerne or sucrose to provide a range of SOM values from 0 to approximately 20%. A natural Ferrosol soil was also used to assess the instrument's performance and was not subjected to these preparation methods but was instead sampled from the field and prepared according to standard practices (SM) for analysis by LECO combustion, PXRF and the new Z-Plane instrument. Three different trials were conducted, trial 1 employed the typical method for PXRF analyses where sample vials are filled to a predetermined depth (1.5 cm in our case) and analyzed without further treatment. Trial 2 utilized a method where BD and depth of samples were controlled and characterized via pre-analysis compaction to assess effects on measurements (SM). Trial 3 utilized the same method as trial 1 with the exception that compaction was regulated using a transducer (SM). Trial 2 and trial 3 samples were also analyzed using a TerraSpec Vis-NIR device (ASD Inc.-United States of America). Various combinations of the multidimensional PXRF, Vis-NIR and single dimensional Z-Plane data were integrated and modeled using partial least squares regression (PLSR) or simple linear regression (SLR) and model performances were evaluated for different combinations of the data (SM).

Evaluated using United States Environmental Protection Agency (USEPA) soil data quality criteria (USEPA, 1998), results were on average quantitative for trial 1. Average coefficients of determination (R2) were high and ranged between 0.92-0.93 and average relative standard deviations ranged between 19.64%-27.49%. For trial 2, a post compaction sample depth>1.2 cm was empirically determined not to affect Z-Plane measurements and all samples were verified with a sample depth greater than this threshold (SM). Significance assessment P value cutoffs were adjusted to 0.01 from the typical 0.05 utilized in soil sciences to account for the multiple comparisons drawn across different soil/surrogate combinations. Experimental repeatability was high (all replicate regression comparison P values 0.23) (SM). There was a consistent soil type effect across both trials (all P values<0.01) with higher Z-Plane counts associated with the lighter textured Cambisol and the sand as compared with the heavy clay textured Vertisol (SM). Organic matter surrogate did not show a significant effect on sensor response when BD was not controlled [trial 1] (all P values>0.01); however, surrogate type did exert a significant effect on detected responses when BD was controlled [trial 2] (all P values<0.01) (SM). Sensor drift was minimal throughout the experiments (SM). Analytical repeatability in measurements was high for triplicate analysis conducted on an adopted standard without re-homogenization (RSD<1%) (SM). The trial 3 method (normal trial 1 method with transducer regulated compaction) was first tested on the Cambisol-Lucern soil for SOM ranging at low concentrations from 0 to approximately 5% and it produced a better and tighter regression than what was produced in trials 1 and 2. Trial 3 was then conducted on the natural Ferrosol soil samples producing quantitative data using simple linear regression. Of the different combinations of data used for soil organic content determination, utilizing the PXRF data in conjunction with the Z-Plane data resulted in the highest quality results.

With the ushering of the maker revolution (Anderson, 2013; Hatch, 2014) the cost of prototyping scientific instrumentation has decreased considerably enabling scientists to inventively and economically attack some of the world's biggest problems (Kwon and Lee, 2017; Sedlak, 2018) such as climate change. Despite room for potential enhancements to this primary prototype and method (SM), on average and across all trials, the Z-plane instrument produced volumetric SOM data via simple linear regression that was comparable with costlier superficial Vis-NIR multivariate instrumentation. The Z-Plane sensor effectively enabled parallel acquisition of volumetric SOM data and elemental compositions via PXRF. On average, the Z-Plane instrument attachment prototype outperformed our Vis-NIR device (TerraSpec-PLSR) and was constructed at a cost of approximately 100 U.S. dollars (USD) which is much lower than what one might expect to pay for scientific equipment capable of quantifying SOM. Foregoing the PXRF device and its associated data, we estimate that a standalone version of this instrument possessing its own X-ray generator can be produced at an additional cost of approximately 300 USD (Science Buddies Staff, 2017). The maker revolution and the associated availability of online resources, integrated circuits, sensors, electronic components, 3D printing and circuit board development capabilities offer scientists an avenue to develop specialized instrumentation pushing the frontiers of science at a lower monetary burden (American Association for the Advancement of Science (AAAS) and Jarvis, 2011; Anderson, 2013; Hatch, 2014; Kwon and Lee, 2017; Science Buddies Staff, 2017; Sedlak, 2018). We use our low-cost instrument attachment as evidence of this and direct attention to its excellent regression reproducibility and soil specific linearity of response to variations in SOM The device could potentially empower scientists with the ability to perform low cost, rapid, high throughput analyses and may be especially useful in cases where dense site characterization (Taylor et al., 2004) of soil organic content is desired such as for SOC sequestration and the UNFCCC's climate change mitigation monitoring and benchmarking purposes.

Sample Preparation: Vertisol, Cambisol, sand, Ferrosol

The procedures for soil sample pre-preparations are described below.

The soil sample (Vertisol, Cambisol, sand) is grinded in a large ball mill for 1 hour to de-clump and homogenize the soil.

The milled soil sample is sieved using a mechanical sieve. The last sieve in the stack is a 250-micron mesh. This is done to isolate the <250-micron fraction of soil and to further homogenize the soil sample.

The sieved soil sample is dried in a soil drying oven at 105-110 degrees Celsius for 24 hours.

The sample is removed from the oven and further homogenized using a riffle splitter 5 times (Schumacher et al., 1990).

The sample is ignited at 440 degrees Celcius as recommended by ASTM (2014) for 24 hours.

After ignition, the sample is removed from the oven and allowed to sufficiently cool before being homogenized once again 5 times using a riffle splitter (Schumacher et al., 1990). The sample should now be homogenized and clear of any organic matter.

The sample is then transferred to a plastic container for use in the incremental surrogate addition steps.

Note: Trial 3 used a natural Ferrosol soil and was not subjected to these preparation procedures. As is common for soil analyses, the Ferrosol was sampled from the field, dried at 40 degrees Celsius for 48h, sorted to the <2 mm fraction, and crushed to <100-microns in preparation for subsequent PXRF, Z-Plane and LECO analyses (Wilson et al., 2017).

Sample Preparation: Incremental Surrogate Addition (Vertisol, Cambisol, sand)

Trials 1 and 2 were conducted at different points in time but these instructions apply to both cases with the exception that for trial 2, sample vials were filled completely.

The procedures for incremental organic matter addition to soils is as follows:

Draw a line associated with a 15 mm sample depth on the XRF analysis vials.

Fill a vial to the indicated line with an ignited and homogenized soil sample (Vertisol, Cambisol, sand). Cap and label the vial with the associated soil type, surrogate, and organic matter content of the soil.

Pour the remaining ignited soil into a previously weighed vessel with a cap which will serve as a mixing vessel for subsequent steps. The new vessel weight minus its empty weight is the weight of soil contained within the vessel.

Sieve the surrogate you will be using (commercial powdered white sucrose or powdered Lucerne) with a 250-micron sieve. Retain the <250-micron fraction for subsequent steps.

Using the equation employed by Ravansari and Lemke (2018) prepare the next incrementally spiked sample by placing the soil vessel on the scale. Prepare the next sample by adding a sufficient amount of surrogate to the mixing vessel to increase soil organic matter content by the desired percentage. The difference in vessel weight before and after surrogate addition is the weight of the surrogate added. The relevant equation employed by Ravansari and Lemke (2018) is as follows.

$$OM'=((OM*W)+S)/(W+S)$$

Where OM' is the sample organic matter fraction after surrogate addition, OM is the organic matter fraction of the sample prior to organic matter addition, W is the weight of the sample prior to organic matter addition and S is the weight of the surrogate added to the sample.

Cap the vessel and shake sample to mix the added surrogate. This acts as a premix step.

Pour the vessel contents onto a square piece of construction paper for homogenization. Carefully give the cap and vessel light taps on the construction paper to ensure complete transfer of the sample to the paper. Roll the sample over on itself 20 times to homogenize the sample (Piorek, 1998).

Transfer a homogenized aliquot of the sample into a new PXRF analysis vial filling it to the 15-mm line. Label the vial with the associated soil type, surrogate, and organic matter content of the soil. Transfer the rest of homogenized sample back to the mixing vessel.

Repeat steps 5 through 9 until the sample has been spiked to the desired organic matter content (20%).

Construction of Compactor Apparatus for Trial 2 Analyses

A compactor apparatus was constructed to control and characterize sample depths and densities. It was constructed using the plunger end of a syringe with its black rubber removed. An XRF analysis vial was cut from the bottom and placed on a smooth plastic surface. It was filled with epoxy resin and the syringe plunger was inserted into the vial. The resin was left to harden and then the XRF analysis vial was cut away using a razor, this created a mold of the analysis vial interior consisting of a smooth base. Trial 2 samples used this plunger to compact samples.

Transducer Apparatus for Trial 2 and 3 Analyses

An apparatus was constructed and employed for trial 2 samples to deliver a set amount of energy to the samples prior to compaction using the previously described compactor apparatus. The delivery of this energy to the samples serves as a compaction step itself prior to pushing the plunger on the compactor because it removes potential air pockets and increases uniformity across samples. A surface transducer (GD003) manufactured by Shenzhen Huihongsheng Electronics Co (China) was wired up to a generic LM386 module and connected to laptop audio output.

Python code was used to generate a signal which was sent the transducer, the signal consisted of a 5 second 300 hz burst and then a linear chirp signal was applied which varied between 1-500 hz over 40 seconds. This code can be found in the supplemental text. Trial 3 also employed this apparatus using a shorter cylindrical vessel.

Analysis of Samples (Trial 1 and Trial 3)

Trial 1 and trial 3 procedures are identical except for step 4. No duplicated measurements were conducted for trial 3. Trial specific instructions are provided below (namely step 4 and step 7).

1. Uncap and place an X-Ray thin film mylar cover 1.5 µm [SOMAR-FILM Micro-Plus Mylar, Sietronics Pty Ltd. (Australia)] over the analysis vial opening and place a rubber band around the analysis vial with four loops positioning the rubber band uniformly at the top edge of sample vial.

2. Cut the excess X-Ray thin film mylar around the rubber band.

3. Give the analysis vial a few shakes using a rolling motion and an up and down motion alternating between the two. The objective is to re-homogenize the sample.

4. Trial 1: Turn over the analysis vial (mylar side down) and give the vial 3 light taps on a wooden surface to remove any air pockets and ensure that the sample is evenly spread out at the top and bottom of the analysis vial.

Trial 3: Turn over the analysis vial (mylar side down) and place it in the previously described transducer apparatus. Run the associated code for the transducer and allow it to finish.

5. Place the analysis vial onto the PXRF analyzer window while giving the vial a push and a twist into the platform grove to ensure that the sample placement is consistent throughout all experiments.

6. Analyze the sample with the PXRF instrument and the attached radiation detector. Note: Analysts should start logging data from the Z-Plane sensor before the PXRF instrument begins analyzing the sample.

7. Trial 1: Perform steps 3 through 6 again to obtain a duplicate measurement of the sample between a re-homogenization event.

Trial 2: No duplicate measurement taken for trial 3.

8. Cap, save and store analyzed samples for potential future experiments.

Analysis of Samples (Trial 2)

This section requires the constructed plunger described in previous sections. Refer to "Construction of Compactor Apparatus for Trial 2 Analyses". Sample vial radius is required for subsequent computations (1 cm). This procedure requires sample vials to be cut from the bottom. In the interest of saving resources, the same vial was re-used between analyses after thoroughly cleaning them with tap water and drying with paper towels. Vials were discarded and new vials utilized for different soil/surrogate combinations. These samples are not sensitive to cross contamination because the analyte is organic matter which is present at the percent levels. In addition, the compactor and vials are made from plastics and polymers and do not absorb water.

1. Cut out the bottom of an analysis vial using a razor (henceforth referred to as the "cut end").

2. Place two sheets of Mylar X-Ray thin film on the plunger's resin and insert the plunger into the cut end of the vial. The Mylar on the plunger serves to inhibit soil from sliding into the area between the analysis vial and resin. Extra Mylar should be cut away.

3. Using a sharp razor create a small slit in the analysis vial at the top edge (opposite cut end) approximately 7 mm away from edge to serve as an air release valve when samples are compacted within the vials.

4. Take note of the prepared compactor mass.

5. Transfer the relevant soil sample into the compactor in preparation for analyses filling it up as much as possible.

6. Take note of the prepared compactor mass again to enable calculation of the soil mass contained within the compactor.

7. Place an X-Ray thin film mylar cover 1.5 µm [SOMAR-FILM Micro-Plus Mylar, Sietronics Pty Ltd. (Australia)] over the analysis vial opening and place a rubber band around the analysis vial with four loops positioning the rubber band uniformly at the top edge of the sample vial.

8. Overturn the sample and place the sample into the transducer apparatus. Run the python code and when finished remove the sample and place the bottom of the sample on a hard table surface. Proceed to apply pressure to compact the sample as much as possible.

9. Analyze the sample using the PXRF and the Z-Plane detector.

10. Remove sample from analysis platform and remove the protective Mylar and rubber band. Return the sample contents to its designated vial for potential future use. Tap lightly to remove compactor contents but do not allow compactor to move.

11. After the compactor has been emptied, determine the mass of the compactor. It will be slightly more than before as there will be negligible remnants within the vial.

12. Fill the compactor with water minimizing meniscus effects visually and determine the mass of the filled compactor. Subtract the filled mass and the empty masses from one another to determine the mass of water. Use this mass of water along with the density of water at 20 degrees Celcius to compute the volume of the compactor.

13. Sample bulk density during analyses can then be computed by diving compactor soil mass by compactor water volume.

14. Sample depths can also be computed from compactor volume by recognizing that the volume of the cylindrical vials are $V=h*pi*r2$. Rearranged for depth this becomes $h=V/(pi*r2)$ where V is the computed compactor volume, r is the vial radius and h is the sample depth.

General Considerations and Notes for Z-Plane Sensor:

A standard should be run periodically throughout experiments and it is recommended that a standard be analyzed between approximately every 10 sample measurements to allow the analyst to check for instrumental drift (Brand and Brand, 2014). The chosen standard is the 0% organic matter sand sample from the trial 1 sand-sucrose experiment and was analyzed throughout all experiments.

The PXRF is operated at 40 kv and 10 microamp settings. The PXRF is a Bruker Tracer III-SD.

The PXRF and Z-Plane analyses are conducted for a duration of 3 minutes each.

A freeware serial monitoring program called "Cool Term" is used to log data however many serial monitors exists and can be used instead. The radiation detector is wired to an Arduino Mega 2560 Rev 3 which is connected to a laptop via USB connection. The serial monitoring program is used to log data from the communications port. Data from the sensor is sent to the Arduino and the Arduino sends the information to the laptop. The relevant code for Z-Plane detector operation is provided in the supplementary text.

Vis-NIR Processing

A Terraspec Vis-NIR device was used to perform 3 replicate scans (10 seconds per scan) on trial 2 and 3 samples. The handheld probe was not moved between replicate scans. The samples were poured on a sheet of paper and gently flattened with a piece of wood that was wrapped with saran wrap. Saran wrap was also used as a protective barrier between the contact probe and the samples. The splice corrected replicate Vis-NIR data was averaged into a single spectrum using python code. The manufacturer specified Terraspec spectral resolution (Full width half maximum) is 3 nm at 700 nm, 6 nm at 1400 nm and 6 nm at 2100 nm. The bins associated with noise were not used in the modelling, i.e. Terraspec bins [350-2500 nm] were cut down to [402-2220 nm] (Ellinger et al., 2019). RS3 software version 6.0.7 was used to acquire the spectra for the samples. ViewSpec Pro software version 6.0.9 was used to perform splice processing. TSG Professional software version 7.0.1.062 was used to export spectral data to csv format for subsequent modelling. Partial least square regression (PLSR) and leave one out validation was performed in Matlab version R2017b (performance statistics summarized in Table 1).

Partial Least Squares Regression

Models were created from the various (Vis-NIR, PXRF, Z-Plane) spectral data using partial least squares regression with leave one out. Models were constructed using the processed Vis-NIR data, raw PXRF spectral data consisting of 2048 bins associated with energy range of 0-40 kV, and Z-Plane sensor data (single dimensional). Various blends of these data were modelled using PLSR and the methods used to integrate the disparate data for the various combinations are discussed.

The previously described processed Vis-NIR spectral data was modeled using PLSR without further treatment.

The previously described PXRF spectral data was modeled using PLSR without further treatment.

The Z-Plane counts alone were not modeled using PLSR but were modeled using simple linear regression instead.

Typically, analytes are directly predicted using multidimensional data in conjunction with PLSR. Integration of disparate multidimensional data (PXRF and Vis-NIR spectra) and single dimensional Z-Plane data was achieved using a novel multivariate version of the Ravansari-Lemke calibration method, referred to as RL-PLSR. The multidimensional spectral data was used to predict correction coefficients for multiplication to Z-Plane SLR determined organic measurements to correct them and get them to where they ought to be. It is a method for mitigating variability in the SLR using the information contained in the spectra. To maintain independence of the calibrations and validations and avoid a circular logical fallacy, these correction coefficients were computed from the SLR (using stepwise leave one out) and predicted via PLSR (also using leave one out). The predicted coefficients were then applied to the SLR determined analyte measurements (Fig. S 5). RL-PLSR is essentially a method for fine tuning anchored baseline SLR analyte measurements using multidimensional data (where the multidimensional data is used to predict correction coefficients via multivariate methods for subsequent application to baseline values obtained via simpler methods). The multivariate version of the Ravansari-Lemke calibration method may be usefully applied to different circumstances where baseline values are available (e.g. RL-multivariate to predict coefficients for application to baseline PXRF rendered total concentrations for bioavailability prediction). This method was used for the "Z-Plane+PXRF", "Z-Plane+Vis-NIR", and "Z-Plane+PXRF+VisNIR" combinations. The integration of disparate PXRF and Vis-NIR spectra are discussed below.

Integration of the disparate PXRF and VIS-NIR spectra was achieved by summing all bins in each spectra and dividing each individual bin by the summed total for each spectra. The spectra thereby retain their shapes and the information contained within but are now on an even playing field with each other. The two disparate spectra were then concatenated for subsequent use in PLSR (PXRF+Vis-NIR) or RL-PLSR (Z-Plane+PXRF+Vis-NIR) procedures.

The number of components used for the various multivariate PLSR models were determined by balancing model parsimony and minimizing the mean square prediction error of the model.

Refrigeration of Prepared Samples

Trial 1 samples were analyzed after their creation but were not stored in a refrigerator. Over time this may lead to changes in SOM content for those samples due to mineralization processes. While not in use, trial 2 samples were stored in a refrigerator at all times after their creation to prevent potential mineralization. It is recommended that analysts refrigerate prepared samples to preserve them for potential future experimentation.

The mounting platform immobilizes the sensor within the Z-plane for consistency throughout experiments. The groove in the mounting platform fits the analysis vials and the objective of the groove is to ensure consistent sample placement throughout the experiments because variations in sample distance from the sensor can affect results.

A closeup picture of the mounting platform and sensor can be viewed in Fig. S 3 and Fig. S 4. The objective of the mounting platform is simply to immobilize the sensor within the Z-plane for consistency throughout experiments. The groove in the mounting platform fits the analysis vials and the objective of the groove is to ensure consistent sample placement throughout the experiments because variations in sample distance from the sensor can affect results.

Transducer Signal Code (Python)

This code was used for the previously discussed surface transducer.

```
import pyaudio
import numpy as np
from scipy.signal import chirp
p = pyaudio.PyAudio( )
fs = 350000
x = np.linspace(0, 5, 1750000)
y = chirp(x, f0=300, f1=300, t1=5, method='linear')
z = y.astype(np.float32).tobytes( )
t = np.linspace(0, 40, 14000000)
w = chirp(t, f0=1, f1=500, t1=40, method='linear')
q = w.astype(np.float32).tobytes( )
stream = p.open(format=pyaudio.paFloat32,
    channels=1,
    rate=fs,
    output=True)
stream.write(z)
stream.write(q)
stream.stop_stream( )
stream.close( )
p.terminate( )
```

Statistics

Minitab version 18.1 was used for regression significance testing of replicate regressions constructed for trial 1, for regression significance testing of different soil-surrogate responses, and for control chart generation to check for sensor drift. Matlab version R2017b was used for PLSR modeling of the Vis-NIR data, RSD determinations for all regressions, and some plot preparation and presentation.

Excel 2016 was used for some table and plot preparation/presentation in addition to basic arithmetic procedures.

Table S 3 summarizes the equations employed in the computations of the metrics presented in Table 1 and Table 2 of the main text.

A 0% SOM sand sample was adopted as a standard and was analyzed regularly throughout the experiments to check for sensor drift (Brand and Brand, 2014; Kenna et al., 2011). A control chart was constructed to track the sensor's response to the adopted standard, it was constructed using Minitab statistical software and is displayed in Fig. S 6. Two outliers were identified which were beyond control limits for the sample average value. Outliers are not deemed to be a result of sensor drift but rather due to human operator inconsistent taps as elucidated in the discussion section.

To assess analytical repeatability under identical conditions the adopted standard was run in triplicate without re-homogenization between analyses resulting in a coefficient of variation (CV) of <1%.

A Horowitz curve was constructed comparing trial 1 20% Cambisol-sucrose sample residual as a function of its sample depth. Sample depths were controlled using the method from trial 2. Residuals were computed using the Cambisol regression from trial 1. Empirically, based on the Horowitz curve a sample depth beyond 1.2 cm should not affect Z-Plane sensor measurements. The 1.2 cm sample depth threshold was computed by performing a first order derivative test on the fitted second order polynomial regression to identify its critical point. The 1.2 cm threshold was adopted as the critical threshold depth for all soil-surrogate combinations because it was later determined that the sensor's height is approximately 1.2 cm from the PXRF analysis platform reinforcing this empirical finding (i.e. if the entirety of the sensor height is covered by a sample's depth then sample depth should not make a difference in the rendered Z-Plane counts).

For all regression significance tests, P values<0.01 are considered significant. The P value has been adjusted from the typical 0.05 to 0.01 to account for the multiple comparisons drawn within the experiments.

Trial 1 regression significance testing was performed on regressions constructed using replicate measurements on the same samples between re-homogenization events to assess repeatability (n=31 vs 31). These tests revealed no significant differences between comparisons (all P>0.23).

Trial 1 regression significance testing comparing different soils-surrogate combinations was performed on the 31 available data points which were generated by averaging the two available replicate measurements for every sample (n=31 vs 31). Results indicate a significant soil type dependent response (all P<0.001) but surrogate type effects are not significant (all P>0.01).

Trial 2 regression significance testing comparing regressions for different soil-surrogate combinations was performed on the 21 available data points which include analytical replicates both with and without re-homogenization for the highest and lowest non-zero SOM samples (n=21 vs 21). Results indicate a significant soil and surrogate type dependent response (all P<0.001).

For trial 2 bulk density (BD) was characterized which enabled development of plots relating Z-Plane sensor response to soil BD. There was a strong relationship between soil BD and counts.

Cook's distance is often used to identify potential outliers in simple linear regression (Cook, 1979). For the trial 3 (natural Ferrosol) simple linear regression of Z-Plane counts against SOC, three potential outliers were identified where the computed cook's distances were greater than $4/(n-k-1)$ (where n is the number of samples used to construct the regression and k is the number of independent variables). Of these identified outliers, the single most influential point on RSD was removed from the dataset. A potential cause of outliers within the datasets may be due to the human introduced variability caused by BD alteration when the samples were removed from the transducer for placement into the analysis platform. This highlights another advantage of integrating the transducer into the analysis platform as discussed in the "Transducer Integration" section of these supplementary materials.

Measurement Time

When the sensor is operational, it is continuously streaming data into bins. The samples were analyzed for a total of three minutes however, lower analysis times may yield similar results as depicted in Fig. S 10. Using samples from the sand-sucrose experiment, we show that similar regression coefficients of determination were produced using discrete bin numbers associated with different measurement integration times. This suggests that measurement time can be greatly decreased and opens the possibility of using short X-ray pulses to obtain of soil organic content information.

Standalone Device Embodiment

Amptek's "Cool-X" pyroelectric X-ray generator may be useful in the development of a standalone instrument because the element is approximately the size of a penny (Amptek, 2019) and would be well suited for portable instrumentation (although it may currently be cost prohibitive). Another option is to utilize a relatively inexpensive cathode ray tube and high voltage generator to replace the PXRF component for X-ray generation. Both these options suffer from X-ray flux variability over time and temperature which fluctuate depending on operational circumstances. This variability can perhaps be mitigated by implementing Peltier cooling elements although this solution will require a great deal of power which may not be ideal for current battery technology. Given the relatively high heat capacity of liquid water, another option is to implement water cooling elements whereby a small isolated storage tank of water (~0.5 L) is placed in contact with corrosion resistant thermally conductive cooling elements that are in contact with the heat generating elements. The heat generated from operation would then be transferred to the water and the water could be replaced as needed when it reaches some predefined temperature (instrument could be programmed to monitor water temperature and halt analyses/alert analyst as needed). Another option is to monitor temperatures and X-ray flux using another X-ray sensor placed adjacent to the X-ray source so that the device consists of two separate X-ray sensors. One of the sensors would monitor the flux of X-rays from the source and the other would be used to analyze the sample. Variability in measurements due to variability in the flux of the X-ray source could then be mitigated using the SLR version of the Ravansari-Lemke calibration method (Ravansari and Lemke, 2018). Such a standalone device may also have an integrated transducer at the sample platform to regulate sample compaction.

Transducer Integration

Regulating compaction of the samples was determined to improve results (FIG. 2). Therefore, for the natural soil samples (trial 3) this was achieved by placing normally prepared samples into the transducer apparatus prior to analyses. Vibrating samples can however affect the grain size distribution within the vial because different grain size fractions may sort/vertically stratify within the vial as a function of transducer parameters such as amplitude, frequency and time of operation. Different grain size fractions also have been shown to possess different elemental concentrations. This sorting phenomenon introduces an interesting possibility for potential rapid determination of soil grain size distribution as soil texture was shown to exert a significant effect on detected counts (i.e. sort grain size distribution using transducer and analyze detected counts vertically along vial by employing a mobile Z-Plane sensor with a collimator). If an energy dispersive mobilized Z-Plane detector with collimation is employed, determination of elemental concentrations within different grain size fractions also becomes a possibility. Currently, soil grain size analyses can take up to 16 hours to conduct so adapting PXRF to generate rapid grain size distribution information would be beneficial. These potential issues and opportunities pertain to un-grinded samples however, in preparation for ex-situ analyses, samples are often grinded and so these opportunities are not possible and the stated issues are of concern. These issues can be circumvented entirely by integrating the transducer with the sample holder assembly and seamlessly activating the transducer after having performed PXRF analysis. Implementation of this suggestion would preclude the analysis from being a truly "parallel" analysis however, with manufacturer support this can be a seamless integrated system that produces a great deal of useful soil information than what is currently possible with rapid PXRF instrumentation. Nonetheless, the results of these experiments demonstrate that good calibrations can be developed for soil organic content quantification using the employed methods. Identification of optimal transducer operation time, amplitude and frequency characteristics and transducer effects on PXRF concentration measurements when collimation is implemented between sample and mobilized Z-Plane detector should be explored in future work.

Discussion

The analytical repeatability of the sensor's response was excellent (CV<1%). Similar to PXRF geochemical measurements, much higher variability is observed when samples are disturbed between analyses (Ravansari and Lemke, 2018). This may be due to heterogeneity and/or other potential sources of analytical variability such as sample BD variations when analysis vials are overturned and placed in the analysis platform between re-homogenization events. For trial 1, as is common to solid PXRF analyses, sample vials were overturned and tapped on a clean surface to ensure a smooth PXRF area of analysis and removal of potential air pockets. The method employed for trial 1 is much more convenient, less time consuming, and produced better results as compared to the BD controlled method employed in trial 2. The method employed for trial 1 however, suffers from the potential introduction of additional variability due to inconsistent human taps. To remove the possibility of measurement variation due to inconsistent human taps, trial 3 explored employing the trial 1 method with transducer regulated compaction in lieu of human taps. This greatly improved the quality of the regressions. This may be especially important for this device and method because there is much higher three-dimensionality to the analyses and variable human taps may cause inconsistent compaction and BD variations which in turn affect the counts detected at the Z-plane sensor. This is further highlighted by the control chart where 2 data points were identified as beyond control limits indicating a high degree of random variability events which we attribute to inconsistent operator taps. The outliers indicated by the control chart are interpreted as human inconsistency events as opposed to sensor drift because the experimental measurements conducted between those standard runs still resulted in very high coefficients of determination. The <1% CV achieved between replicate runs without re-homogenization events also hints that the observed variability is due to the re-homogenization or sample placement step. This source of random variability likely exists in the computed regressions as well affecting precision of the method but the trends clearly indicate a good average linear response to increasing SOM content. We thus postulate that precision can be increased and calibrations improved by further controlling such sources of random variability associated with sample vial preparation and placement. This proof of concept device demonstrates the potential feasibility of using an X-Ray sensor in the Z-plane to extract sample information but if low limits of detection and high accuracy are to be achieved, measurement precision must be increased by eliminating random variability.

Nevertheless, the sensor is responding accordingly to variations in soil organic content regardless of surrogate type but there is a strong soil type dependent response observed highlighting the potential viability of site specific calibrations or preset calibrations for popular soil types. Variation in SOM has been shown to cause elementally specific deviation in PXRF geochemical measurement accuracy (Ravansari and Lemke, 2018). These deviations may be accounted for by employing SOM correction procedures described by Ravansari and Lemke (2018). The correction procedures require the quantification of SOM for all samples which is costly and time consuming. This instrument attachment may be used to rapidly and concurrently obtain SOM information during PXRF analyses which can then be used in conjunction with onboard device computers to seamlessly compute and apply appropriate corrections via onboard algorithms. The described process can potentially result in more accurate PXRF geochemical measurements in addition to SOM and SOC information thus advancing the utility of PXRF instrumentation. Where elemental concentrations are not required, the PXRF component of the instrument can be replaced with a simple X-Ray source allowing its operation as a standalone instrument presumably further increasing portability and decreasing costs.

The instrument discussed in this manuscript was developed as a proof of concept for use in the laboratory however, we also suggest the development of a soil specific intrusive instrument attachment for PXRF devices specifically for in-situ applications. It is assumed that in-situ variability in soil moisture may further complicate device performance by affecting SOM determinations. We postulate that these effects may be mitigated by simultaneously quantifying soil water and developing calibrations. Integration of an intrusive soil water probe is thus a potentially welcomed amalgamation because it may facilitate in-situ applications. Soil water has also been shown to decrease in-situ PXRF geochemical measurement accuracy. The integration of a water probe would enable parallel soil water content determination, and corrections to PXRF geochemical measurements could be applied using an analogous extension of Ravansari and Lemke's (Ravansari and Lemke, 2018) SOM corrections adapted to soil water content. Development of a hybrid soil specific PXRF device consisting of an intrusive radiation detector and soil water probe is suggested because this would potentially enable quantification of SOM, soil water content, and more accurate soil elemental concentrations (because elemental concentrations could be corrected for SOM and water contents via streamlined onboard algorithms).

Trial 1 produced quantitative results. Sample vials in trial 1 were filled to a consistent sample depth however, as previously discussed, tapping the vials for PXRF analyses may affect sample compaction and BD which can introduce random variability and ultimately affect measurements. Development of an objective repeatable method and apparatus for controlling compaction uniformly (trial 3) enabled better quantification of soil organic content.

The development of this device presents an interesting opportunity for augmenting of PXRF measurement capabilities because in addition to the potential for SOM corrections which have been discussed, other corrections may be applied as well. Compton normalization and fundamental parameters are calibration procedures which are employed for some PXRF devices and are used to render measurements or otherwise mitigate measurement deviation by accounting for variability in sample matrix composition (USEPA, 2007). The information rendered by this device may be potentially used in a similar fashion to increase accuracy by mitigating variability in sample matrix composition. Conversely, the PXRF spectra that is simultaneously generated during analyses may be used to increase the attachment's accuracy as well because it can inform algorithms of sample composition for potential accountability. The interplay and advantages of using one device's information to augment the other was explored in this study and should be further explored using both simple and multivariate techniques including fundamental parameters-esque or Compton normalization-esque adaptations. Finally, the sensor employed in this investigation detected incident radiation in the Z-plane irrespective of its energy level (for its sensitive range) however, despite its low cost, it is potentially capable of being employed as a crude energy dispersive detector as well. An interesting extension of this work would be to employ the detector as an energy dispersive sensor to extract further information from samples undergoing X-Ray analyses such as vertical stratification of analytes. Other more advanced energy dispersive sensors such as Amptek's X-123 sensor (Redus et al., 2006; Redus et al., 2009) adapted for employment in the Z-plane could potentially enable enhanced data acquisition and better SOM quantification from samples undergoing PXRF analyses. Employment of a Z-Plane detector may require a redesign of sample vials used for PXRF analyses. A new type of vial is suggested which is comprised of a sidewall or side-stripe which is made of a high a strength polymer or graphene. Such a vial may aide Z-Plane measurements as it will reduce the attenuation and scattering of desirable signals for better detection at the Z-Plane detector. The results of this preliminary work warrant further investigation into the feasibility of such a Z-plane radiation sensor for soil chemical characterization via either generic, soil specific, or site specific parsimonious simple linear regressions, or even standalone and/or mix and matched hybrid multivariate techniques utilizing PXRF spectra and Z-Plane sensor data.

It will be apparent to one with skill in the art that the matter characterization systems and methods may be provided using some or all of the mentioned features and components without departing from the spirit and scope of the present invention. It will also be apparent to the skilled artisan that the embodiments described above are specific examples of a single broader invention which may have greater scope than any of the singular descriptions taught. There may be many alterations made in the descriptions without departing from the spirit and scope of the present invention.

REFERENCES

Adams, W. A., 1973. THE EFFECT OF ORGANIC MATTER ON THE BULK AND TRUE DENSITIES OF SOME UNCULTIVATED PODZOLIC SOILS. Journal of Soil Science 24(1), 10-17.

American Association for the Advancement of Science (AAAS), Jarvis, M., 2011. Science Selects 'Science Buddies' Web site to Win SPORE Award|Available at: https://www.aaas.org/news/science-selects-science-buddies-web-site-win-spore-award [Accessed: 29 Apr. 2019]. (April 29).

Anderson, C., 2013. Maker Movement, Wired. Conde Nast Publications, Inc., San Francisco, pp. 106-n/a.

Assunção, S. A., Pereira, M. G., Rosset, J. S., Berbara, R. L. L., Garcia, A. C., 2019. Carbon input and the structural quality of soil organic matter as a function of agricultural management in a tropical climate region of Brazil. Science of The Total Environment 658, 901-911.

Australia New Zealand Banking Group—ANZ, 2018. Carbon Trading—ANZ|Available at: http://www.anz.com/corporate/markets/carbon-trading/[Accessed: 21 Aug. 2018]. (21-08-2018).

Australian Federal Government—Australia, 2018. Carbon Credits (Carbon Farming Initiative—Measurement of Soil Carbon Sequestration in Agricultural Systems) Methodology Determination 2018—F2018L00089|Available at: https://www.legislation.gov.au/Series/F2018L00089 [Accessed: 21 Aug. 2018].

Bentler, P. M., Mooijaart, A., 1989. Choice of structural model via parsimony: A rationale based on precision. Psychological Bulletin 106(2), 315-317.

DAFWA, 2013. Report card on sustainable natural resource use in Agriculture, Australian Department of Agriculture and Food Western Australia.

Gałuszka, A., Migaszewski, Z. M., Namieśnik, J., 2015. Moving your laboratories to the field—Advantages and limitations of the use of field portable instruments in environmental sample analysis. Environmental Research 140, 593-603.

Hatch, M., 2014. The maker movement manifesto: Rules for innovation in the new world of crafters, hackers, and tinkerers. McGraw-Hill Education New York.

IUSS Working Group, W., 2006. World reference base for soil resources. World Soil Resources Report 103.

Kwon, B.-R., Lee, J., 2017. What makes a maker: the motivation for the maker movement in ICT. Information Technology for Development 23(2), 318-335.

Lal, R., 2006. Enhancing crop yields in the developing countries through restoration of the soil organic carbon pool in agricultural lands. Land Degradation & Development 17(2), 197-209.

Parsons, C., Margui Grabulosa, E., Pili, E., Floor, G. H., Roman-Ross, G., Charlet, L., 2013. Quantification of trace arsenic in soils by field-portable X-ray fluorescence spectrometry: Considerations for sample preparation and measurement conditions. Journal of Hazardous Materials 262(Supplement C), 1213-1222.

Potts, P. J., West, M., 2008. Portable X-ray Fluorescence Spectrometry: Capabilities for in Situ Analysis. RSC Pub.

Ravansari, R., Lemke, L. D., 2018. Portable X-ray fluorescence trace metal measurement in organic rich soils: pXRF response as a function of organic matter fraction. Geoderma 319, 175-184.

Reeves, D. W., 1997. The role of soil organic matter in maintaining soil quality in continuous cropping systems. Soil and Tillage Research 43(1), 131-167.

Rouillon, M., Taylor, M. P., 2016. Can field portable X-ray fluorescence (pXRF) produce high quality data for application in environmental contamination research? Environmental Pollution 214(Supplement C), 255-264.

Rouillon, M., Taylor, M. P., Dong, C., 2017. Reducing risk and increasing confidence of decision making at a lower cost: In-situ pXRF assessment of metal-contaminated sites. Environmental Pollution 229, 780-789.

Rumpel, C., Amiraslani, F., Koutika, L.-S., Smith, P., Whitehead, D., Wollenberg, E., 2018. Put more carbon in soils to meet Paris climate pledges. Nature 564.

Saini, G. R., 1966. Organic Matter as a Measure of Bulk Density of Soil. Nature 210(5042), 1295-1296.

Science Buddies Staff, 2017. How to Build an X-ray Machine|Available at: https://www.sciencebuddies.org/science-fair-projects/project-ideas/Phys_p083/physics/how-to-build-an-x-ray-machine # summary [Accessed: 28 Apr. 2019]. (April 28).

Sedlak, D. L., 2018. Disruptive Environmental Research. Environmental Science & Technology 52(15), 8059-8060.

Soriano-Disla, J. M., Janik, L. J., Viscarra Rossel, R. A., Macdonald, L. M., McLaughlin, M. J., 2014. The Performance of Visible, Near-, and Mid-Infrared Reflectance Spectroscopy for Prediction of Soil Physical, Chemical, and Biological Properties. Applied Spectroscopy Reviews 49(2), 139-186.

Taylor, P. D., Ramsey, M. H., Potts, P. J., 2004. Balancing Measurement Uncertainty against Financial Benefits: Comparison of In Situ and Ex Situ Analysis of Contaminated Land. Environmental Science & Technology 38(24), 6824-6831.

UNFCCC, 2016. Paris Agreement—Status of Ratification-|UNFCCC—United Nations Framework for Convention on Climate Change|Available at: https://unfccc.int/process/the-paris-agreement/status-of-ratification [Accessed 21 Aug. 2018]. (21-08-2018).

USEPA, 1998. Environmental technology verification report. Field portable X-ray fluorescence analyzer. Metorex XMET 920-P and 940, EPA/600/R-97/146, United States Environmental Protection Agency.

van Groenigen, J. W., van Kessel, C., Hungate, B. A., Oenema, O., Powlson, D. S., van Groenigen, K. J., 2017. Sequestering Soil Organic Carbon: A Nitrogen Dilemma. Environmental Science & Technology 51(9), 4738-4739.

Viscarra Rossel, R. A., McGlynn, R. N., McBratney, A. B., 2006. Determining the composition of mineral-organic mixes using UV-vis-NIR diffuse reflectance spectroscopy. Geoderma 137(1), 70-82.

Wang, D., Chakraborty, S., Weindorf, D.C., Li, B., Sharma, A., Paul, S., Ali, M. N., 2015. Synthesized use of VisNIR DRS and PXRF for soil characterization: Total carbon and total nitrogen. Geoderma 243-244(Supplement C), 157-167.

B. A. Schumacher, K. C. Shines, J. V. Burton, M. L. Papp, Comparison of Three Methods for Soil Homogenization. Soil Science Society of America Journal 54, 1187-1190 (1990).

ASTM, ASTM Method D2974-14: Standard Test Methods for Moisture, Ash, and Organic Matter of Peat and Other Organic Soils. (2014).

B. R. Wilson, D. King, I. Growns, M. Veeragathipillai, Climatically driven change in soil carbon across a basalt landscape is restricted to non-agricultural land use systems. Soil Research 55, 376-388 (2017).

R. Ravansari, L. D. Lemke, Portable X-ray fluorescence trace metal measurement in organic rich soils: pXRF response as a function of organic matter fraction. Geoderma 319, 175-184 (2018).

S. Piorek, in Current Protocols in Field Analytical Chemistry, V. Lopez-Avila et al., Eds. (Wiley, 1998), chap. Section 3B.

N. Brand, C. Brand, Performance comparison of portable XRF instruments. Geochemistry: Exploration, Environment, Analysis, 2012-2172 (2014).

M. Ellinger, I. Merbach, U. Werban, M. Lieβ, Error propagation in spectrometric functions of soil organic carbon. SOIL Discuss. 2019, 1-25 (2019).

T. C. Kenna et al., Evaluation and calibration of a Field Portable X-Ray Fluorescence spectrometer for quantitative analysis of siliciclastic soils and sediments. Journal of Analytical Atomic Spectrometry 26, 395-405 (2011).

R. D. Cook, Influential observations in linear regression. Journal of the American Statistical Association 74, 169-174 (1979).

Amptek, Amptek.com. (2019). COOL-X X-Ray Generator—Amptek—X-Ray Detectors and Electronics. [online] Available at: https://www.amptek.com/products/x-ray-sources/cool-x-pyroelectric-x-ray-generator [Accessed 24 Aug. 2019]. (2019).

USEPA, "EPA Method 6200 Field Portable X-Ray Fluorescence Spectrometry for the Determination of Elemental Concentrations in Soil and Sediment," (United States Environmental Protection Agency, 2007).

R. H. Redus, J. A. Pantazis, T. J. Pantazis, A. C. Huber, B. J. Cross, Characterization of CdTe detectors for quantitative X-ray spectroscopy. IEEE Transactions on Nuclear Science 56, 2524-2532 (2009).

R. Redus, A. Huber, J. Pantazis, T. Pantazis, D. Sperry, in Nuclear Science Symposium Conference Record, 2006. IEEE. (IEEE, 2006), vol. 6, pp. 3794-3797.

J. Wetterlind, B. Stenberg, Near-infrared spectroscopy for within-field soil characterization: small local calibrations compared with national libraries spiked with local samples. European Journal of Soil Science 61, 823-843 (2010).

C. Kilbride, J. Poole, T. R. Hutchings, A comparison of Cu, Pb, As, Cd, Zn, Fe, Ni and Mn determined by acid extraction/ICP-OES and ex situ field portable X-ray fluorescence analyses. Environmental Pollution 143, 16-23 (2006).

The invention claimed is:

1. An apparatus comprising:
   a radiation source configured to irradiate a sample;
   an electric field sensor configured to detect an electric field of the sample during or after sample irradiation by the radiation source, at least one property of the electric field being altered by the sample irradiation; and
   an onboard computer communicably coupled to the electric field sensor and radiation source, the onboard computer configured to determine one or more sample properties based on the electric field of the sample, the sample properties including at least one of physical or chemical composition of the sample.

2. The apparatus in claim 1 wherein the radiation source produces a monochromatic or polychromatic flux of radiation possessing energies in a singular or plurality of regions of the electromagnetic spectrum.

3. The apparatus in claim 1 further comprising a wavelength dispersive crystal used to control incident radiation energy from the radiation source onto the sample.

4. An apparatus comprising:
   an X-ray fluorescence spectrometer configured to scan a sample;

at least one of an electric field sensor placed proximal to the sample configured to scan the sample by detecting an electric field of the sample during or after sample irradiation by the X-ray fluorescence spectrometer, at least one property of the electric field being altered by the sample irradiation, and an X-ray radiation detector placed proximal to the sample configured to scan X-ray radiation traversing the sample;

a frame configured to control a distance between the sample and at least one of the X-ray fluorescence spectrometer, electric field sensor, and X-ray radiation detector; and an onboard computer communicably coupled to the X-ray fluorescence spectrometer and at least one of the electric field sensor and the X-ray radiation detector, the onboard computer being configured to determine one or more sample properties based on at least one of the electric field and the X-Ray radiation traversing the sample, the sample properties including at least one of physical or chemical composition of the sample.

5. The apparatus in claim 4 wherein an electromechanical transducer is communicably coupled with the one or more processors and is activated by the one or more processors at least one of before, during, between or after analyses.

6. The apparatus in claim 4 wherein the frame supports a core and the base of the frame is mobilized with a motor that is communicably coupled to the one or more processors which activates the motor to move the core longitudinally at least one of before, during, between or after analyses.

7. The apparatus in claim 4 wherein a spectroscopy system is communicably coupled to the one or more processors and scan the sample, the information from the spectroscopy system is used to render one or more sample properties.

8. The apparatus in claim 4 wherein the X-ray fluorescence spectrometer is portable.

9. The apparatus in claim 8 wherein a soil water sensor is placed proximal to the sample analysis area and is communicably coupled with the onboard computer.

10. The apparatus in claim 4 wherein the frame is modularly linkable with at least one of the X-ray fluorescence spectrometer, electric field sensor, and X-ray radiation detector.

11. The apparatus in claim 4 wherein a radiation source is placed proximal to the sample and is communicably coupled with and activated by the one or more processors.

12. The apparatus in claim 4 wherein the distance between the sample and at least one of the X-ray fluorescence spectrometer, electric field sensor, and X-ray radiation detector are controlled by placing the samples into a cavity or groove.

13. The apparatus in claim 4 wherein the one or more processors are communicably coupled to a mobile phone or tablet.

14. The apparatus in claim 13 wherein data is transmitted from the apparatus to the mobile phone and to a network connected nontransitory computer database.

15. The apparatus in claim 14 wherein the mobile phone or tablet further transfer one or more of the associated sample properties wirelessly to a to a non-transitory computer readable medium such as an NFC sticker.

16. The apparatus in claim 4 wherein the data from one or more of the X-ray fluorescence spectrometer, electric field sensor, and X-ray radiation detector are used in at least one of RL-PLSR, PLSR, SLR, or multivariate techniques.

17. A method for determining one or more soil properties comprising the steps of:
a pilot hole is created in a soil profile by inserting and removing a rigid structure possessing a cavity from the soil profile;
at least one of an electric field sensor and an X-ray radiation detector is inserted into the pilot hole;
an X-ray fluorescence instrument is placed proximal to the pilot hole;
the soil proximal to the pilot hole is scanned using the X-ray fluorescence instrument and at least one of the electric field sensor and the X-ray radiation detector; and
the one or more soil properties is determined based on at least one of an electric field of the soil indicated by the electric field sensor and X-Ray radiation traversing the sample indicated by the X-ray radiation detector, at least one property of the electric field being altered by sample irradiation via the X-ray fluorescence instrument, the one or more soil properties including at least one of physical or chemical composition of the soil.

18. The method in claim 17 wherein at least one of the electric field sensor and X-ray radiation detector is partially or wholly covered in a protective barrier.

19. A method for preparing and analyzing a sample comprising the steps of:
at least one of compactional or vibrational energy is applied to the sample thereby reducing sample volume;
the sample is scanned using an X-ray fluorescence spectrometer and at least one of an electric field sensor and an X-ray radiation detector, at least one property of the electric field being altered by sample irradiation via the X-ray fluorescence spectrometer; and
one or more sample properties are determined based on scan data generated by the X-ray fluorescence spectrometer and at least one of the electric field sensor and the X-Ray radiation detector, the sample properties including at least one of physical or chemical composition of the sample.

20. A method for determining sample information comprising the steps of:
irradiating a sample via a radiation source;
scanning the sample via an electric field sensor during or after the irradiation to determine an electric field of the sample, at least one property of the electric field being altered by sample irradiation via the radiation source;
determining one or more sample properties using an onboard computer coupled to the electric field sensor and the radiation source, based on the electric field of the sample, the one or more sample properties including at least one of physical or chemical composition of the sample.

* * * * *